US 7,500,986 B2

(12) United States Patent
Lye et al.

(10) Patent No.: US 7,500,986 B2
(45) Date of Patent: Mar. 10, 2009

(54) EXPANDABLE BODY HAVING DEPLOYABLE MICROSTRUCTURES AND RELATED METHODS

(75) Inventors: Whye-Kei Lye, Charlottesville, VA (US); Michael L. Reed, Charlottesville, VA (US); Kareen Looi, Charlottesville, VA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 563 days.

(21) Appl. No.: 10/521,078

(22) PCT Filed: Jul. 11, 2003

(86) PCT No.: PCT/US03/21754

§ 371 (c)(1),
(2), (4) Date: Aug. 22, 2005

(87) PCT Pub. No.: WO2004/006983

PCT Pub. Date: Jan. 22, 2004

(65) Prior Publication Data

US 2006/0122684 A1 Jun. 8, 2006

Related U.S. Application Data

(60) Provisional application No. 60/395,180, filed on Jul. 11, 2002, provisional application No. 60/421,404, filed on Oct. 24, 2002.

(51) Int. Cl.
*A61F 2/06* (2006.01)

(52) U.S. Cl. ..................................... 623/1.15; 623/1.16

(58) Field of Classification Search ........ 623/1.15–1.46
See application file for complete search history.

(56) References Cited

U.S. PATENT DOCUMENTS

| | | | |
|---|---|---|---|
| 4,856,516 A | 8/1989 | Hillstead | |
| 5,397,355 A | 3/1995 | Marin et al. | |
| 5,514,154 A | 5/1996 | Lau et al. | |
| 5,591,197 A | 1/1997 | Orth et al. | |
| 5,593,434 A | 1/1997 | Williams | |
| 5,681,346 A | 10/1997 | Orth et al. | |
| 5,800,526 A * | 9/1998 | Anderson et al. | 623/1.16 |
| 5,824,053 A * | 10/1998 | Khosravi et al. | 623/1.15 |
| 6,197,013 B1 * | 3/2001 | Reed et al. | 604/509 |
| 6,254,642 B1 | 7/2001 | Taylor | |
| 6,485,496 B1 | 11/2002 | Suyker et al. | |

(Continued)

OTHER PUBLICATIONS

Creel et al., "Arterial paclitaxel distribution and deposition" *Circulation Research* (2000) 86:879-884.

(Continued)

*Primary Examiner*—Suzette J Gherbi

(57) ABSTRACT

Apparatuses, systems and methods for treating a patient by positioning an expandable body (10) having one or more microstructures (14) within a body lumen and penetrating the lumen wall with the microstructures (14). The microstructures are formed in or attached to the lumen through a cacheter or other suitable device. Each microstructure (14) has an end (16) which is attached to the expandable body and a free end (18). Once the apparatus is positioned within the body lumen in a desired location one or more of the microstructures are deployed wherein the free ends project radially outwardly. The free ends of the deployed microstructures penetrate the lumen wall by continued expansion of the body. Additionally, a therapeutic agent may be delivered to the lumen wall by the penetrated microstructures.

28 Claims, 20 Drawing Sheets

U.S. PATENT DOCUMENTS 7,204,847 B1 * 4/2007 Gambale .................. 623/1.14

OTHER PUBLICATIONS

Gonschior et al., "Comparison of local intravascular drug delivery catheter systems" *American Heart Journal* (1995) 130(6):1174-1181.

Hwang et al., "Physiological transport forces govern drug distribution for stent-based delivery" *Circulation* (2001) 104:600-605.

Nakamura et al., "Molecular strategy using *cis*-element 'decoy' of E2F binding site inhibits neointimal formation in porcine ballon-injured coronary artery model" *Gene Therapy* (2002) 9:488-494.

Santini et al., "A controlled-release microchip" *Nature* (1999) 397:335-338.

* cited by examiner

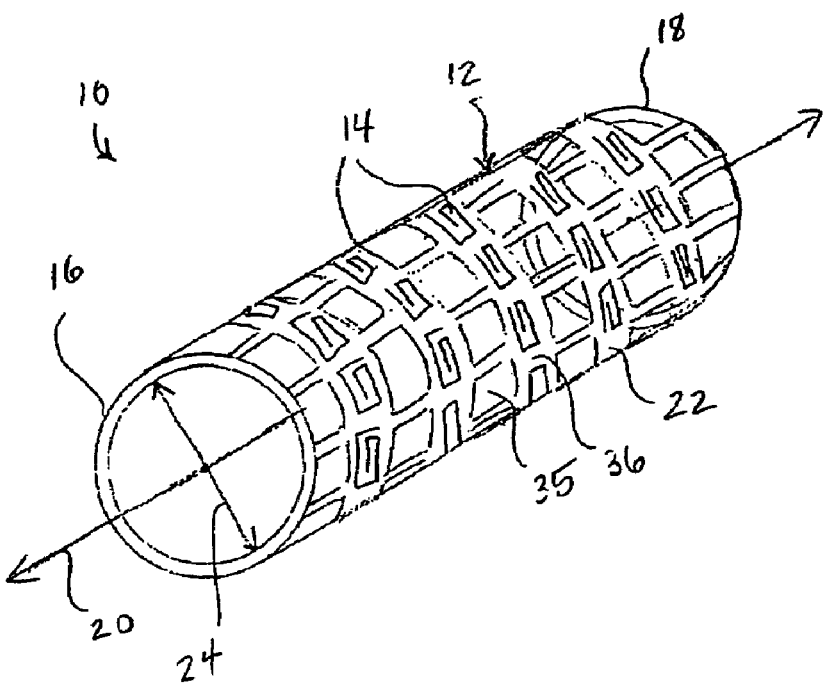
FIG_4
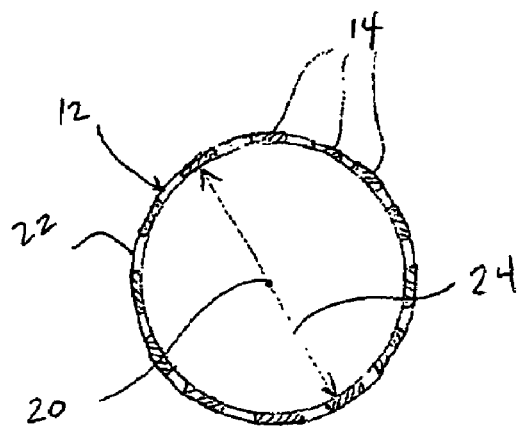
FIG_5A
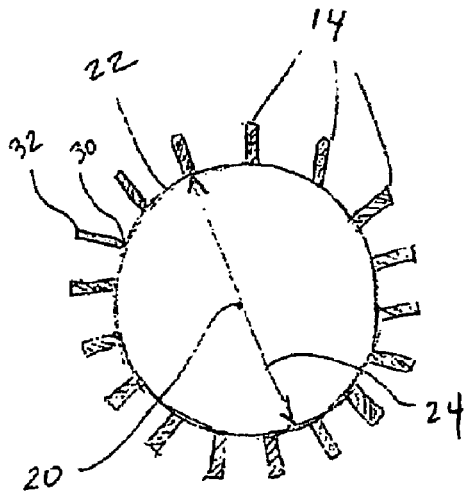
FIG_5B

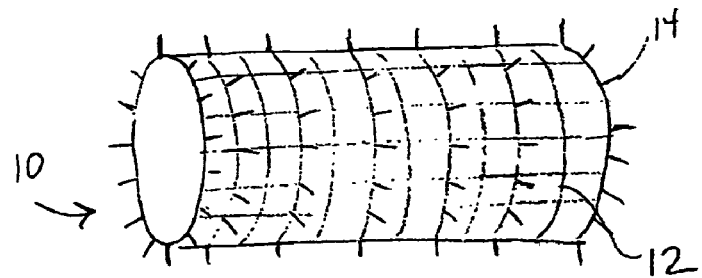
FIG_5C
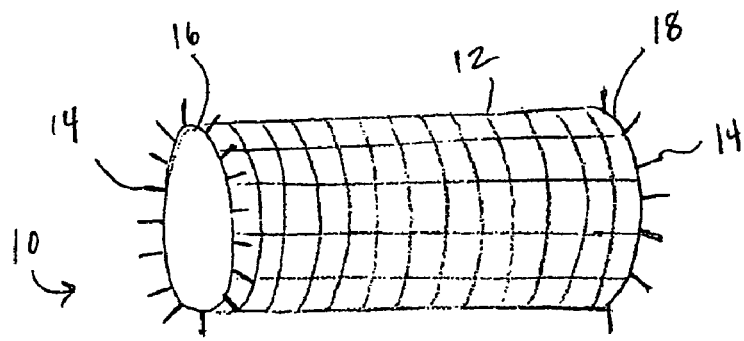
FIG_5D
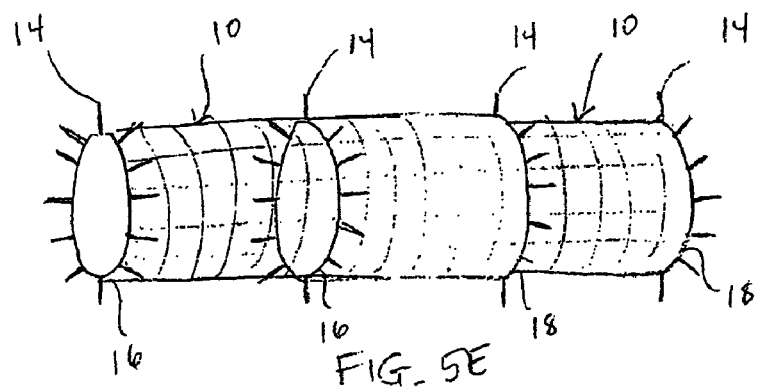
FIG_5E
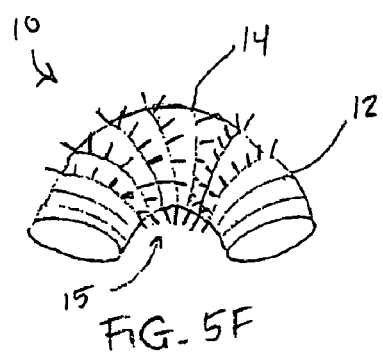
FIG_5F
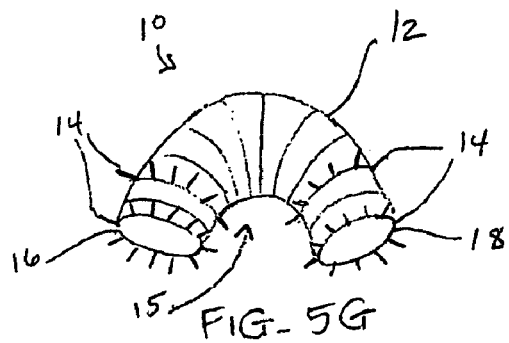
FIG_5G

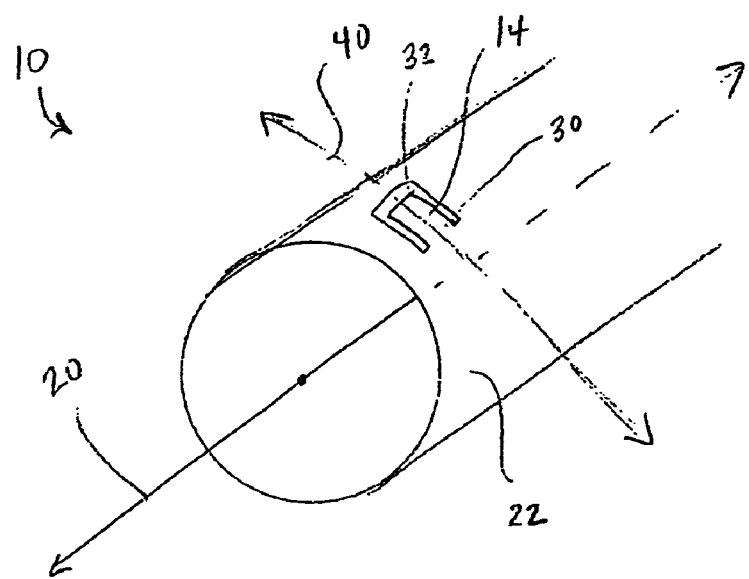
FIG_6A
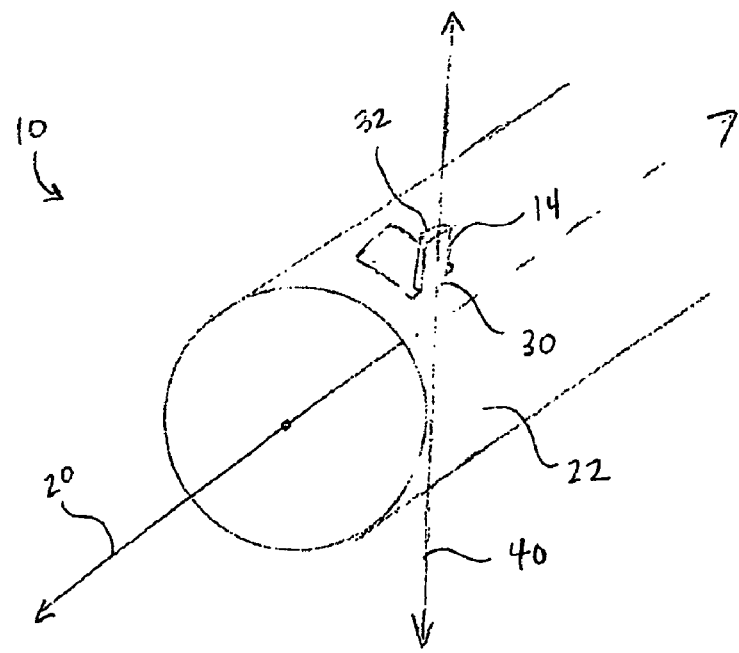
FIG_6B

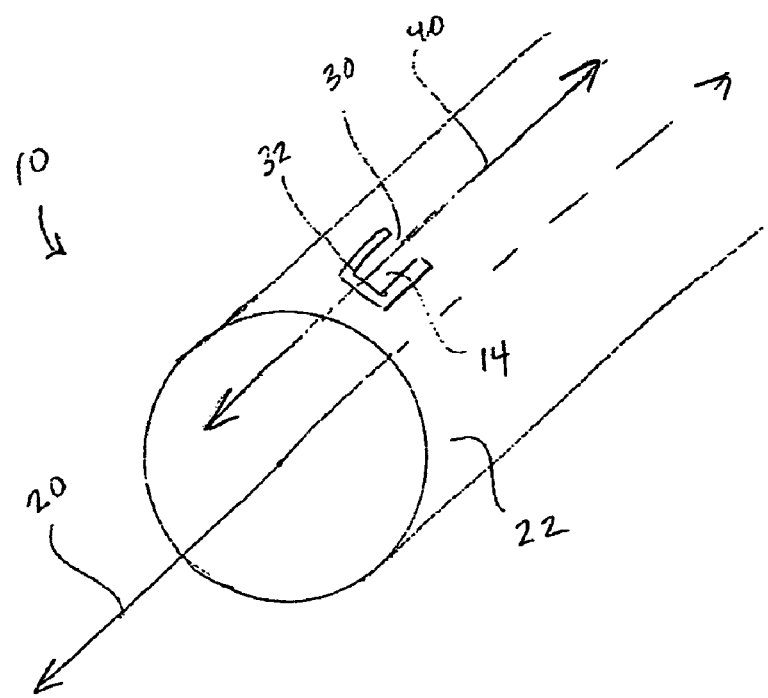
FIG_7A
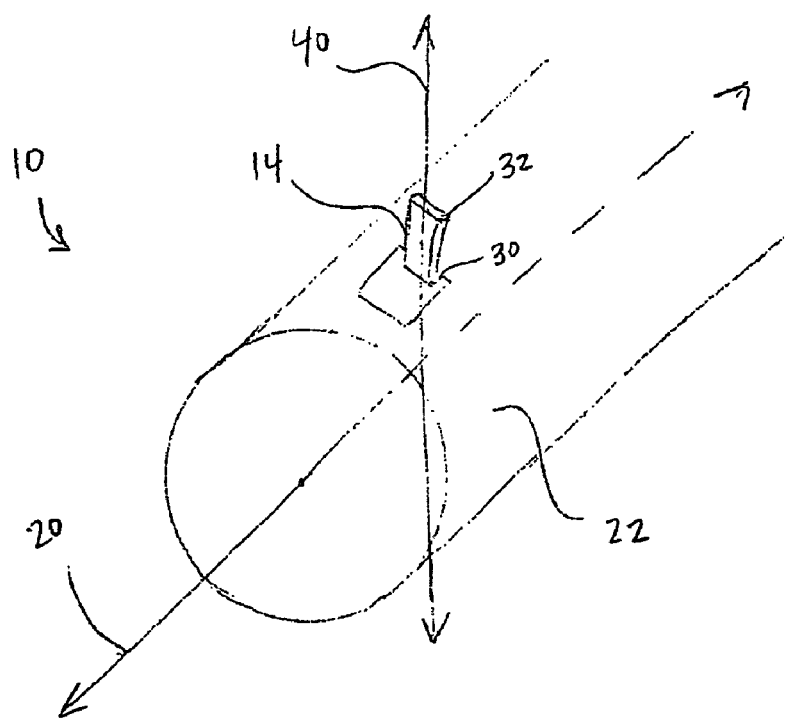
FIG_7B

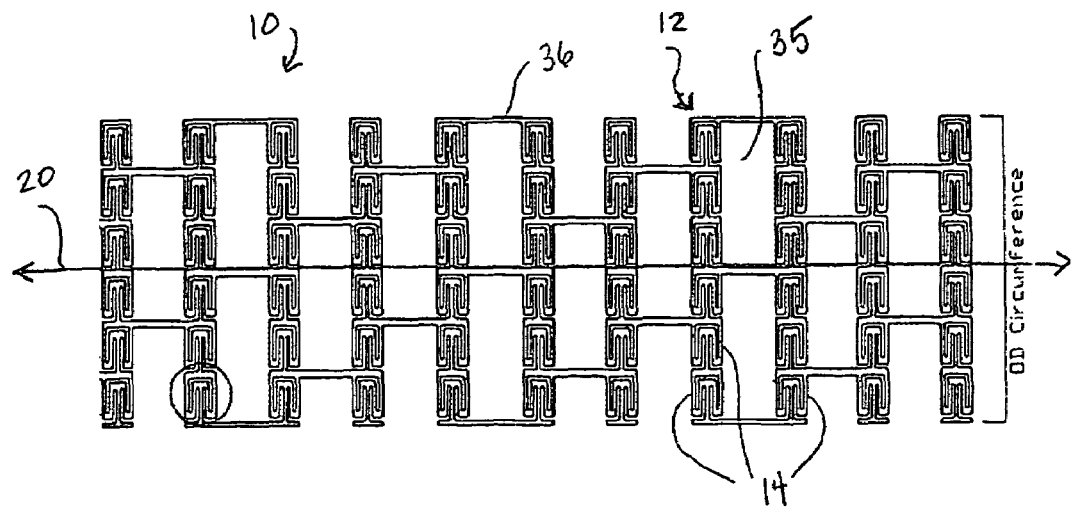
FIG_8
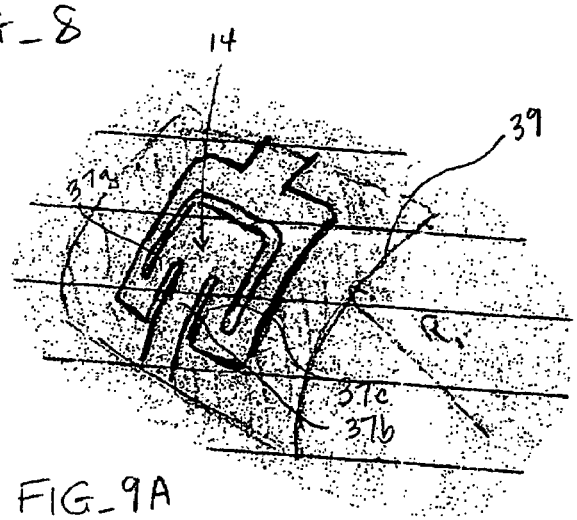
FIG_9A
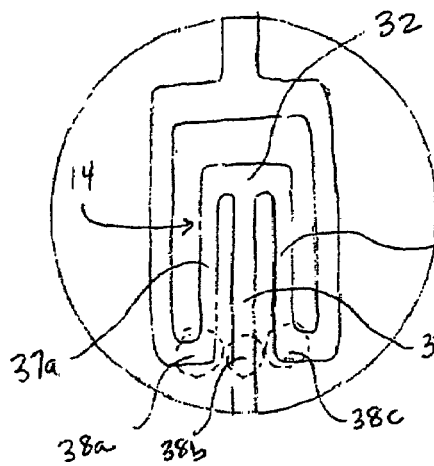
FIG_8A
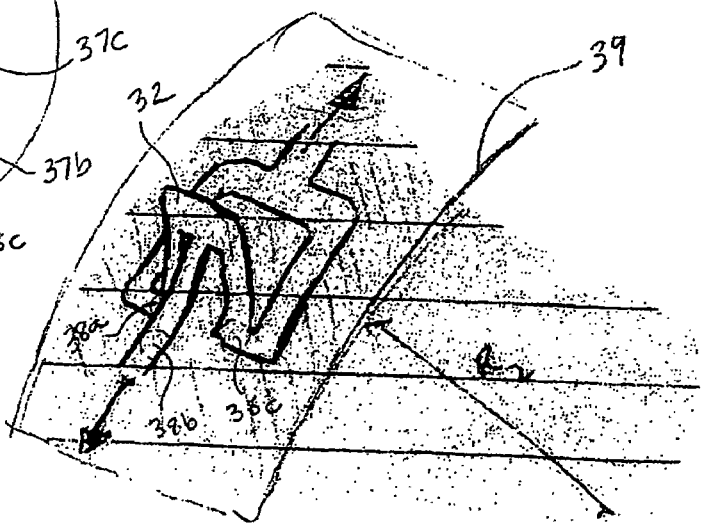
FIG_9B

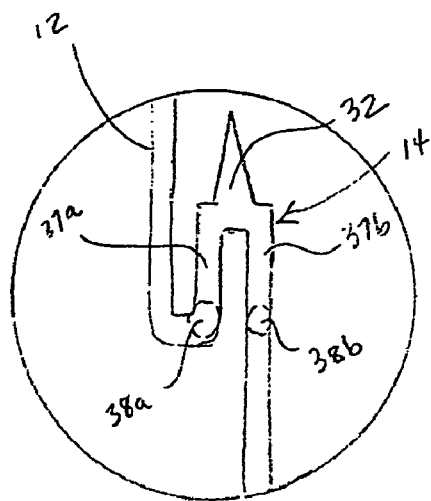
FIG_11A
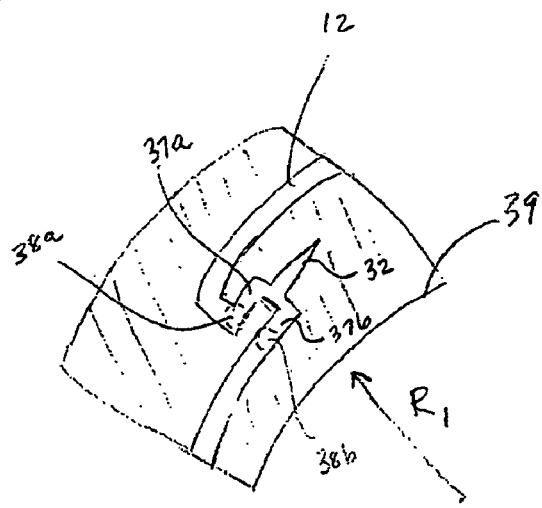
FIG_11B
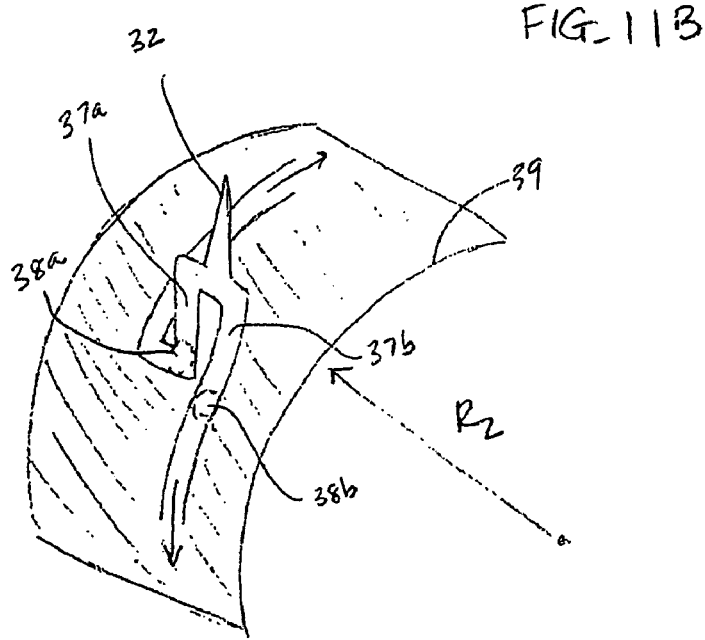
FIG_11C

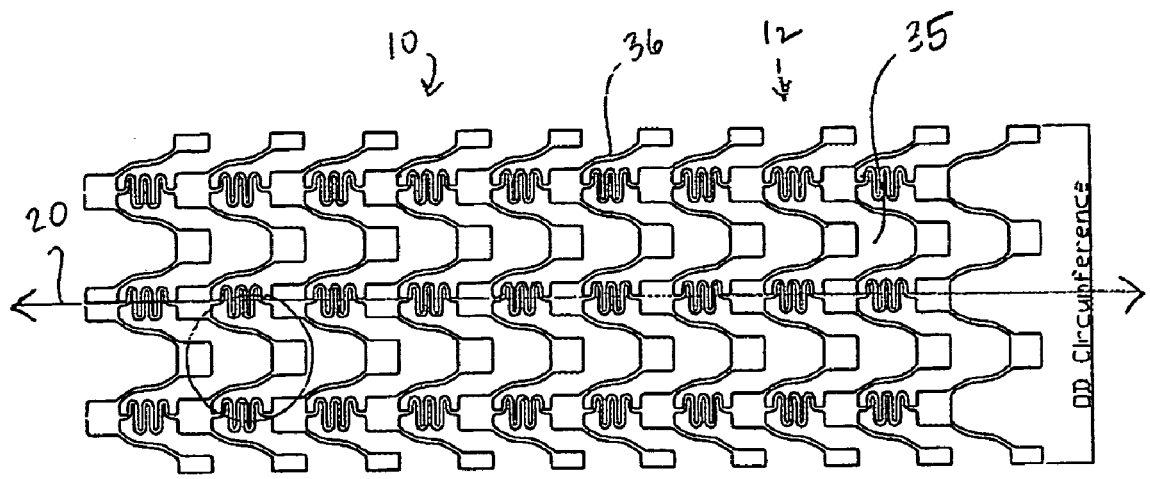
FIG_12
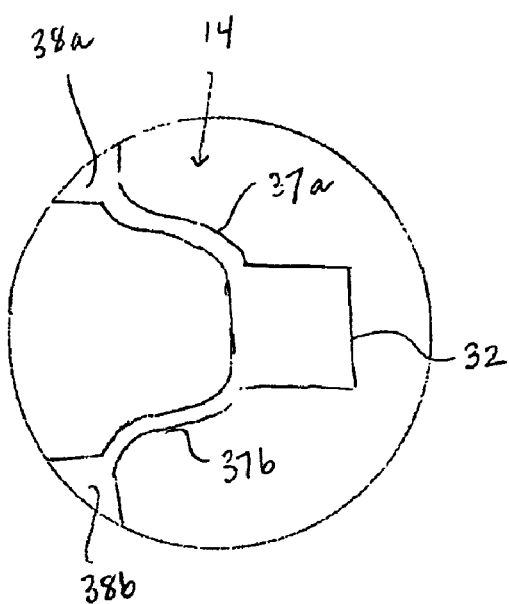
FIG_12A

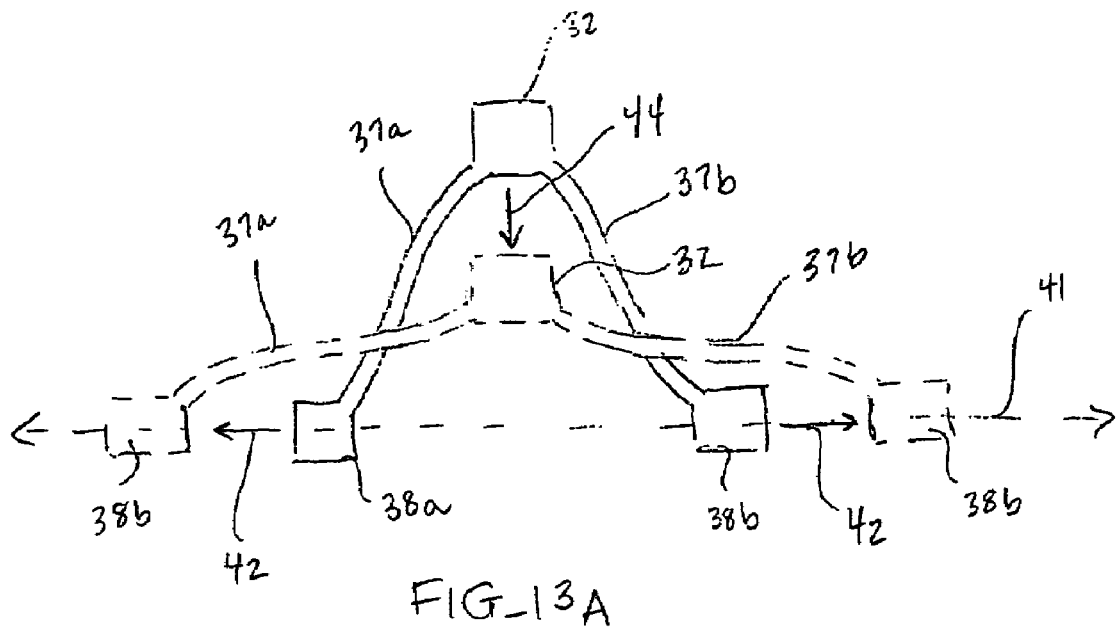
FIG_13A
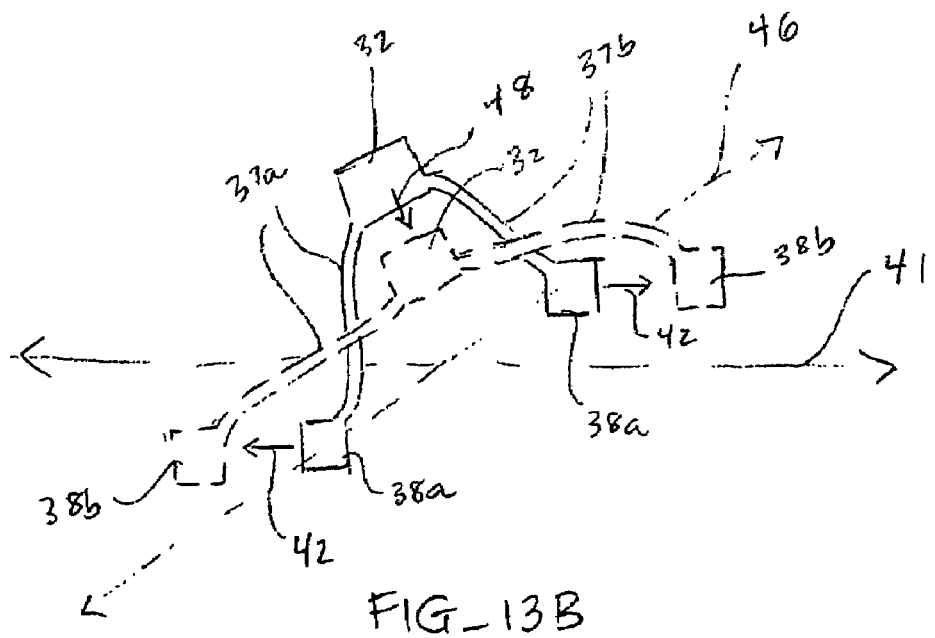
FIG_13B

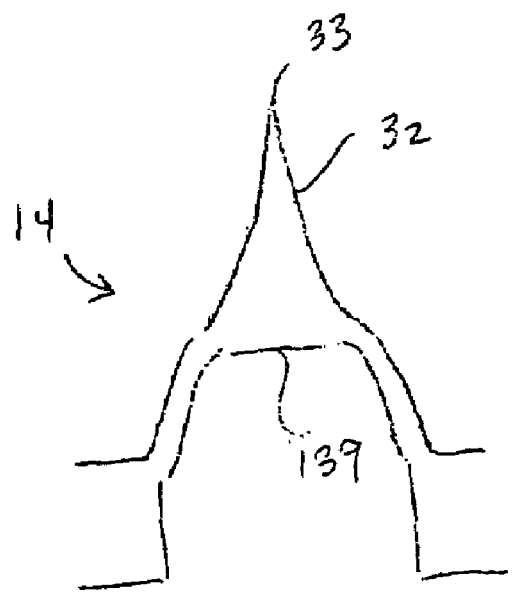
FIG_15A
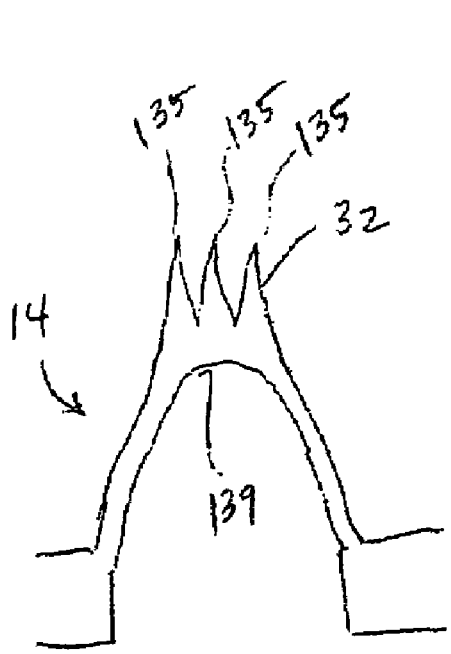
FIG_15B
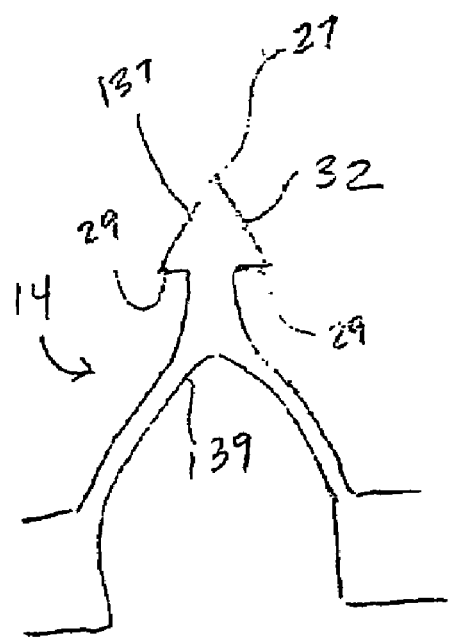
FIG_15C

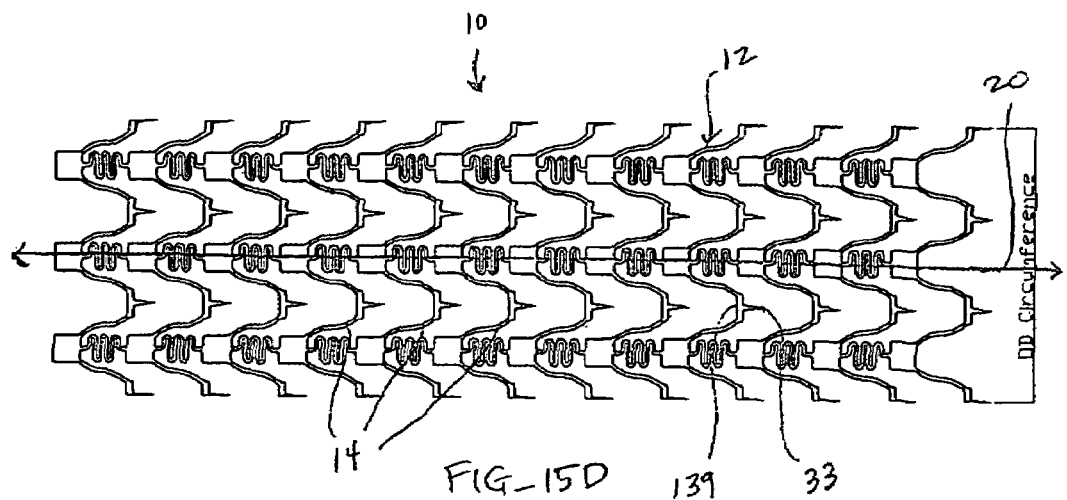
FIG_15D
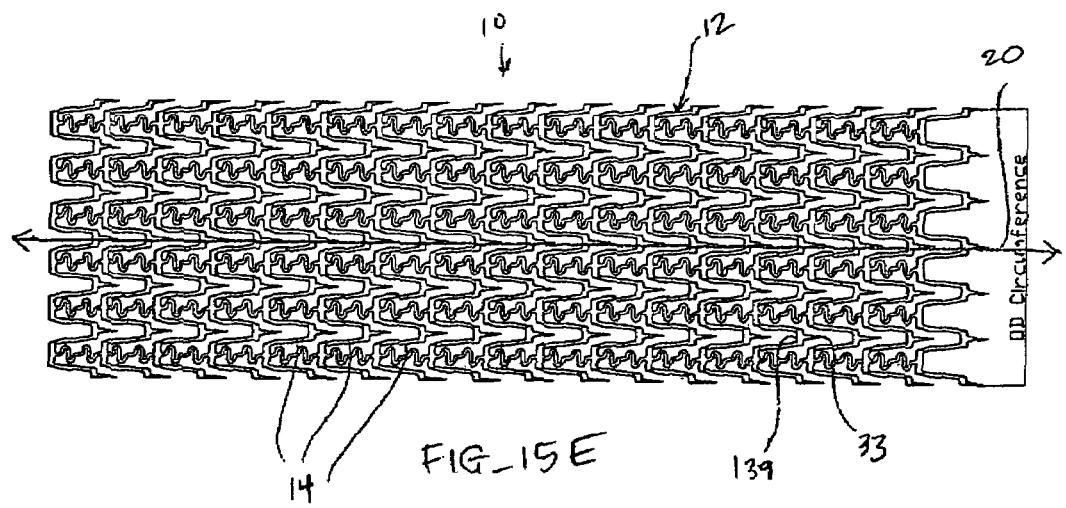
FIG_15E
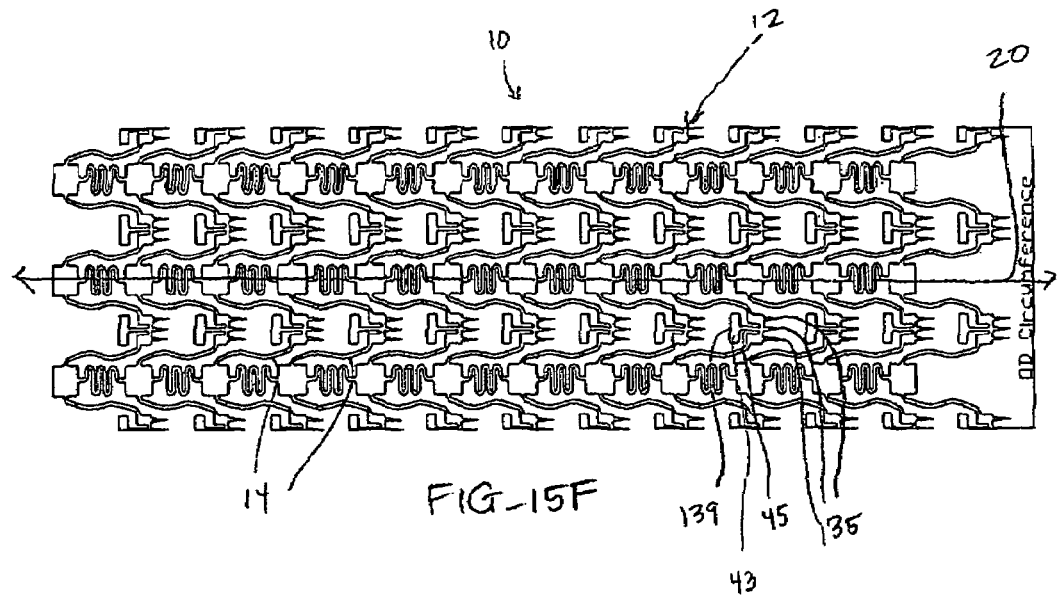
FIG_15F

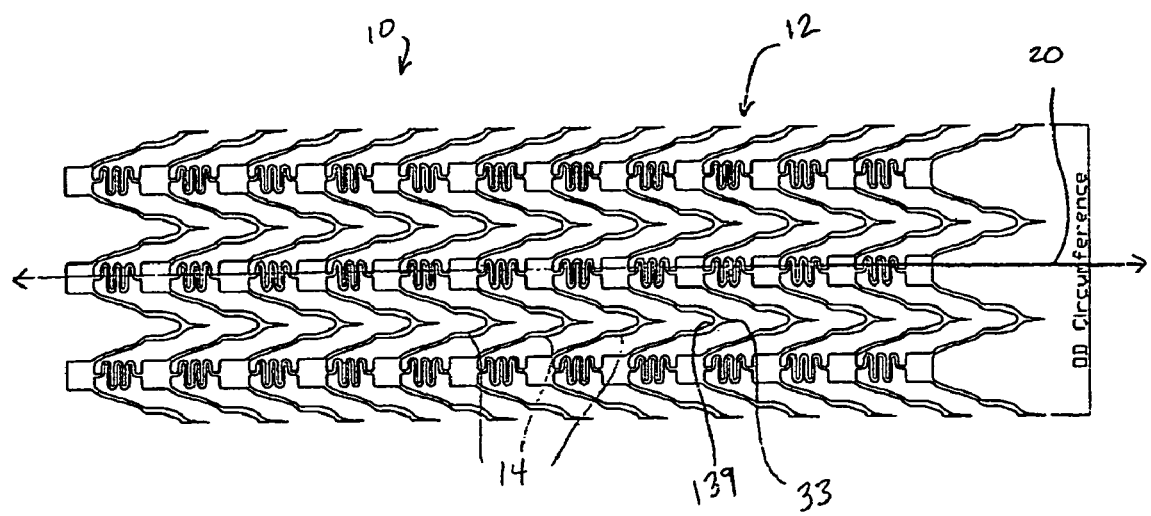
FIG_15G
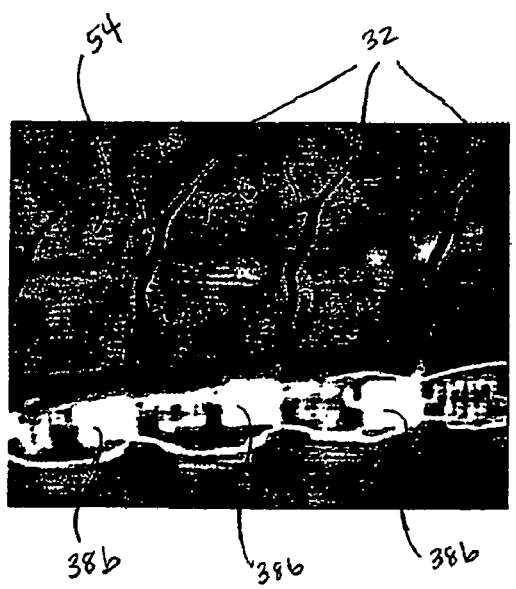
FIG_15H

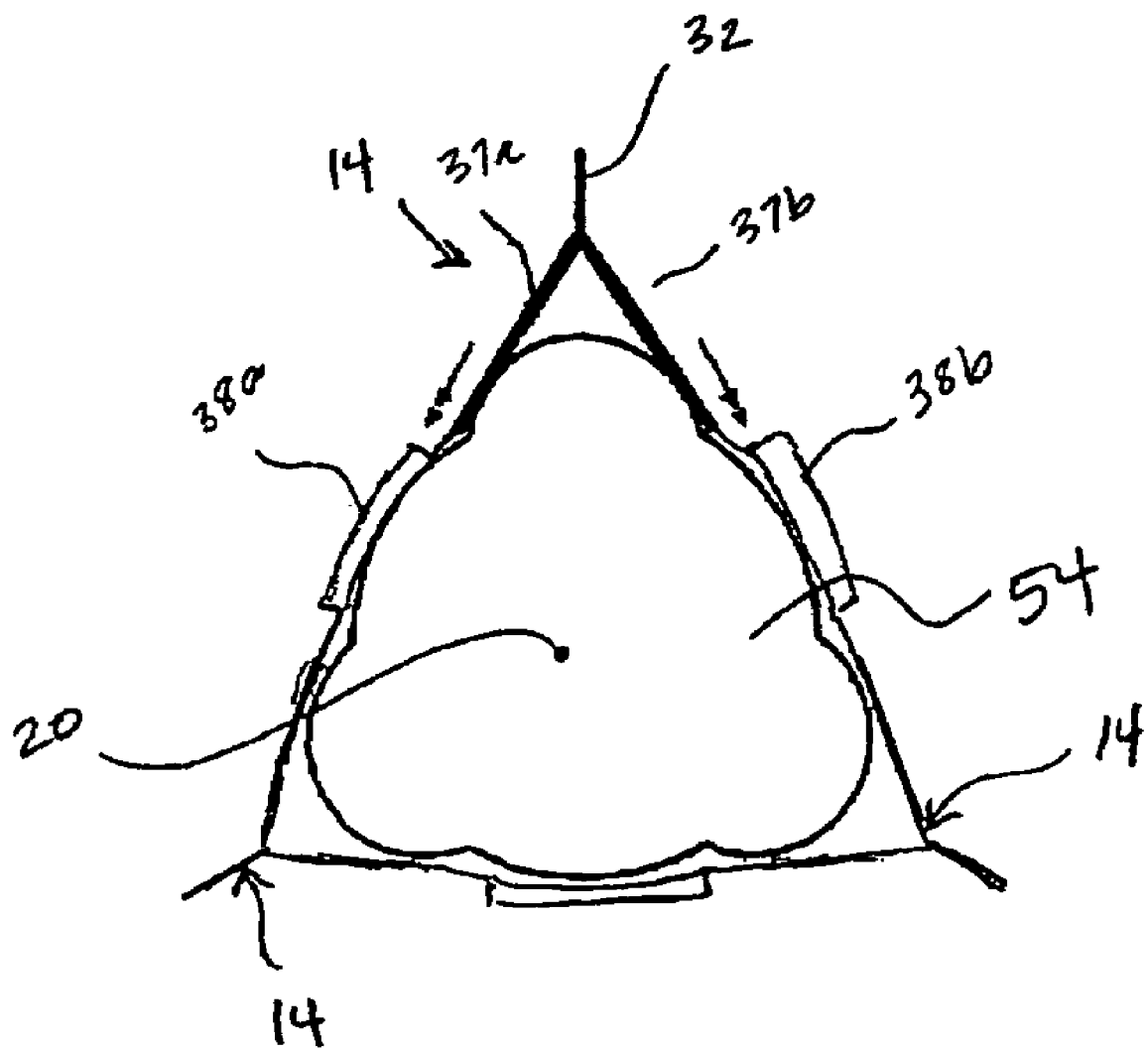
FIG_15 I

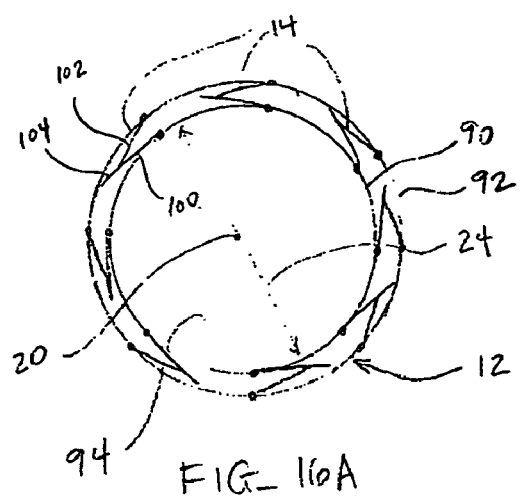
FIG_16A
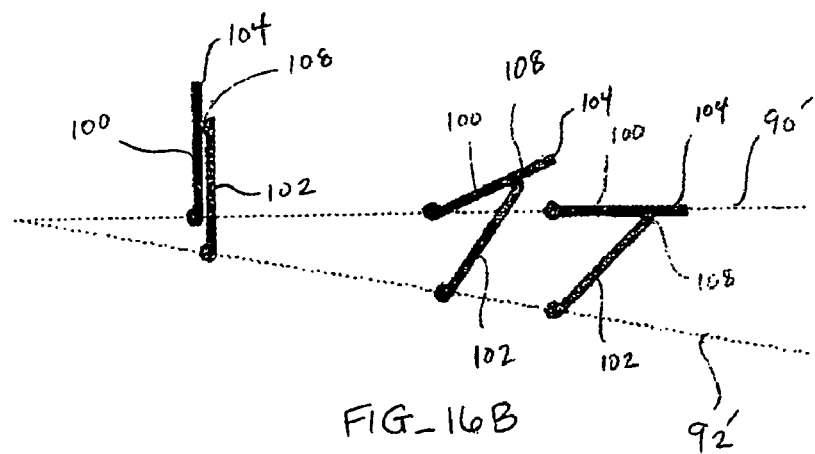
FIG_16B
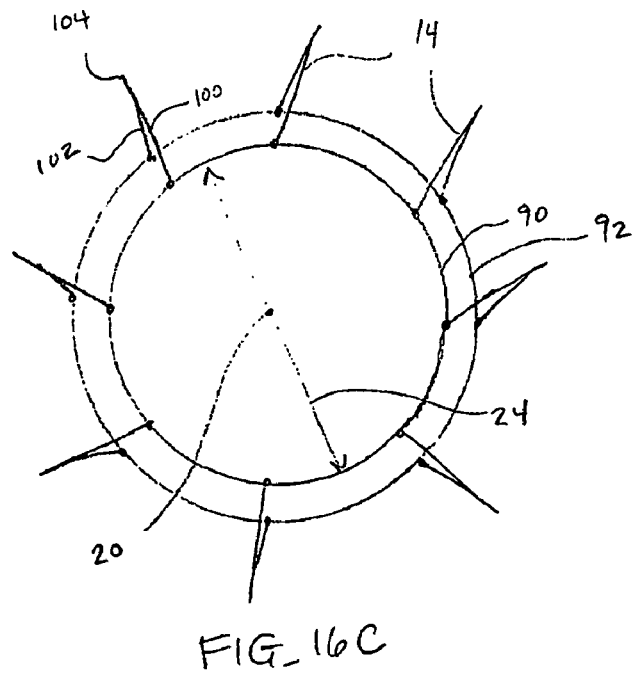
FIG_16C

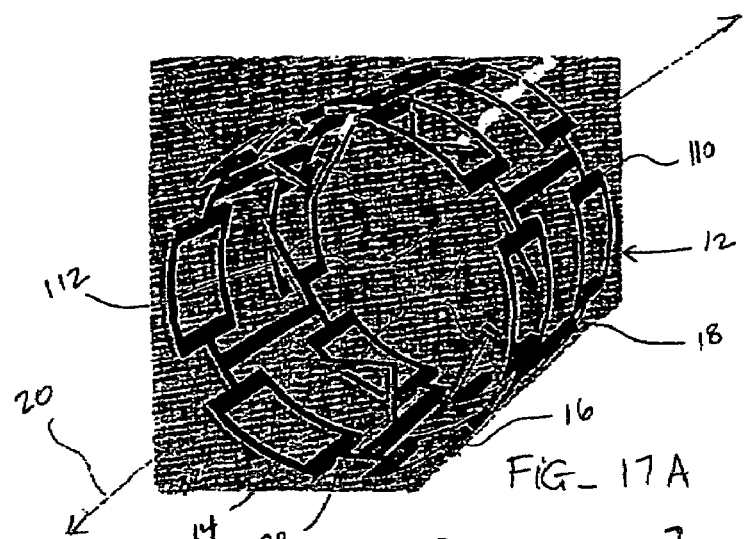
FIG_17A
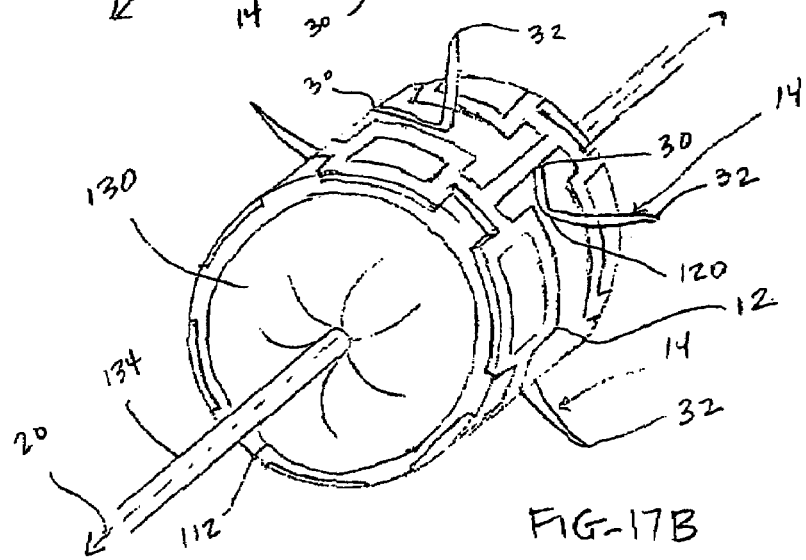
FIG_17B
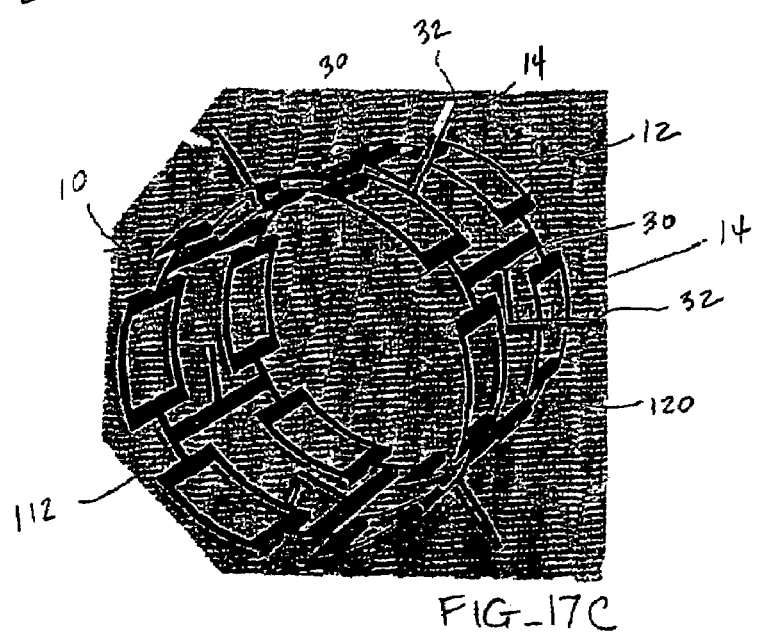
FIG_17C

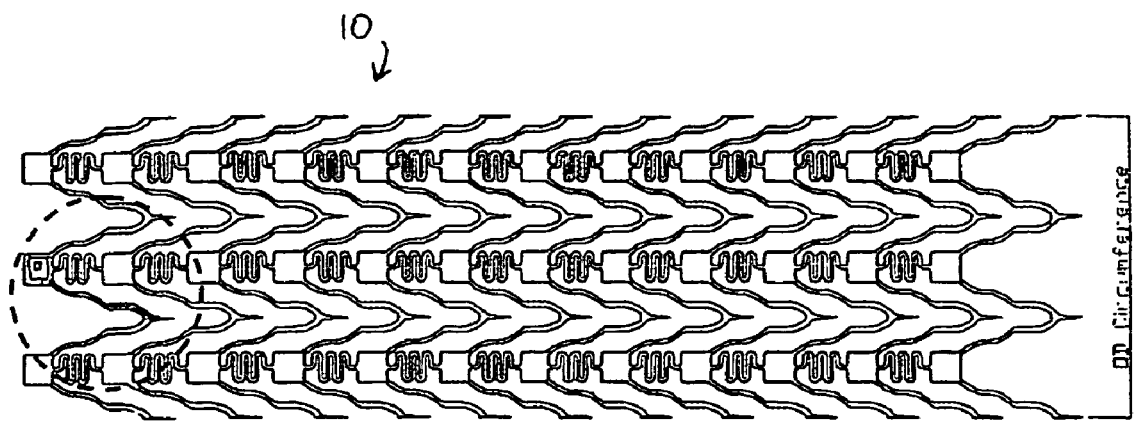
FIG_18
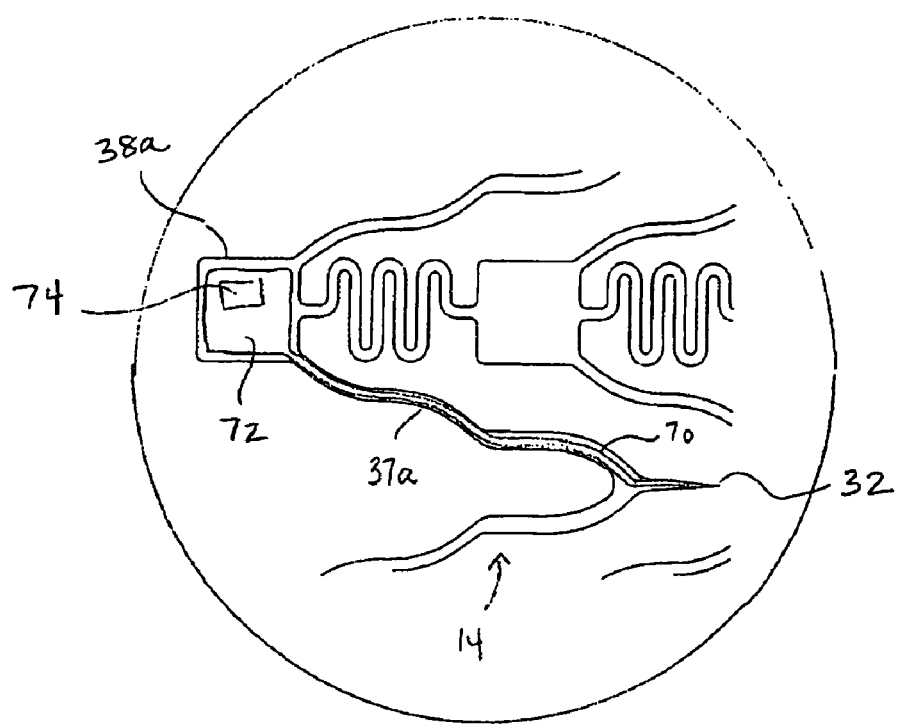
FIG_18A

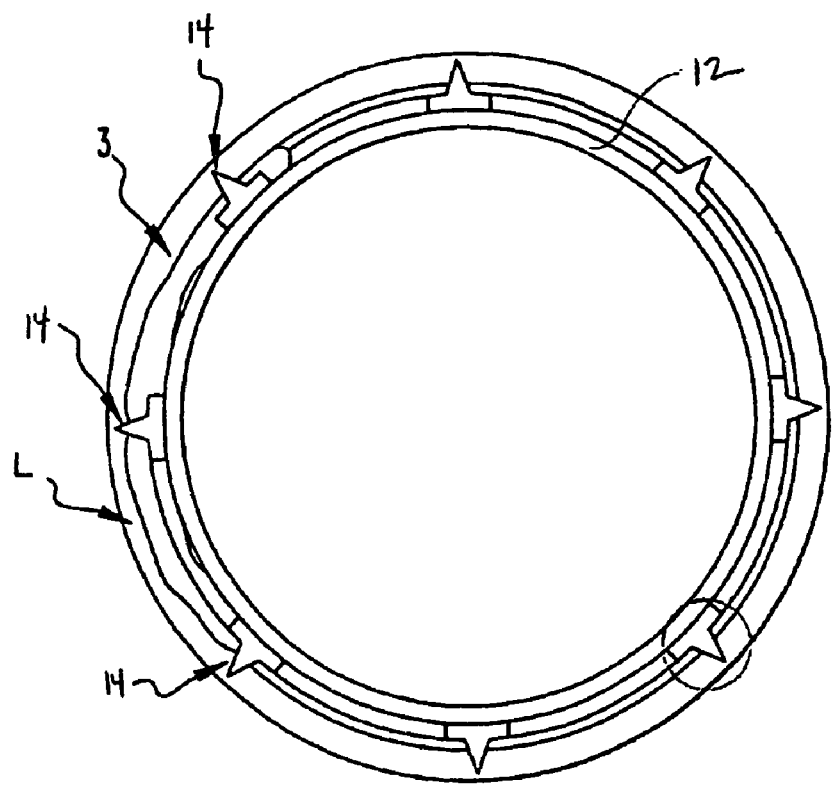
FIG_19
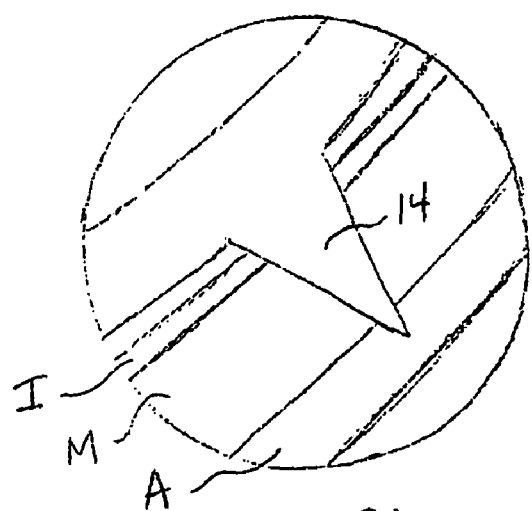
FIG_19A

EXPANDABLE BODY HAVING DEPLOYABLE MICROSTRUCTURES AND RELATED METHODS

CROSS-REFERENCES TO RELATED APPLICATIONS

This application claims the benefit and priority of U.S. Provisional Patent Application No. 60/395,180 filed Jul. 11, 2002, and U.S. Provisional Patent Application No. 60/421,404 filed Oct. 24, 2002, the full disclosures of which are hereby incorporated by reference for all purposes.

Also, this application is related to PCT patent application No. PCT/US03/21754, filed on the same day as this application, the full disclosure of which is hereby incorporated by reference for all purposes.

STATEMENT AS TO RIGHTS TO INVENTIONS MADE UNDER FEDERALLY SPONSORED RESEARCH AND DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK.

NOT APPLICABLE

BACKGROUND OF THE INVENTION

The present invention relates to apparatuses, systems and methods of treating a patient. Particularly, the present invention relates to treating a body lumen. More particularly, the present invention relates to treating a blood vessel, such as in the treatment of heart disease.

Heart disease continues to be a leading cause of death in the United States. The mechanism of this disease is often progressive narrowing of coronary arteries by atherosclerotic plaque which can lead to acute myocardial infarction and disabling angina. Techniques to treat coronary atherosclerosis include percutaneous transluminal coronary angioplasty, (or PTCA, commonly referred to as balloon angioplasty), atherectomy, and coronary stenting. In each of these techniques, a guidewire is threaded to the site of coronary blockage and a treatment catheter is advanced over the guidewire. In balloon angioplasty, the guidewire is passed through the blockage and a balloon catheter is positioned within the blockage. The balloon is then inflated, compressing the atherosclerotic plaque against the walls of the coronary artery. In atherectomy, the treatment catheter is equipped with a cutting device which cuts the plaque away as the catheter is advanced through the blockage. In stenting, a stent, such as a metal or wire cage-like structure, is expanded and deployed against the plaque. Such stenting may be performed after balloon angioplasty or simultaneously with balloon angioplasty wherein the stent is mounted on the balloon. In each of these treatments, compression of the plaque and expansion of the coronary artery, or removal of the atherosclerotic plaque, often restores lumen patency.

Despite the overall initial success of these procedures, many patients undergoing these therapeutic procedures to clear blocked coronary arteries will suffer restenosis (re-blockage) at some point after the initial procedure. Such restenosis may be a manifestation of the general wound healing response. The injury induced by coronary intervention may cause platelet aggregation, inflammatory cell infiltration and release of growth factors, followed by smooth muscle cell proliferation and matrix formation. Thus, intimal hyperplasia due to vascular injury may be involved in the etiology of restenosis.

In an effort to inhibit such restenosis, numerous pharmacological agents and genes have been delivered to such arteries. Although agents and genes have been shown to inhibit restenosis in animal models, many have failed in human trials. One explanation for their failure is that suboptimal doses of agents were used in order to prevent side effects which occur from systemic administration of the higher doses. Consequently, the concept of localized intravascular delivery of therapeutics has become an attractive solution to overcome this limitation.

However, therapeutic agents coating conventional stents may have difficulty controllably passing into the vessel wall. As mentioned, stents mechanically prevent elastic recoil of the compressed plaque. A typical conventional stent is shown in FIGS. 1-2. FIG. 1 shows the coronary stent before expansion and FIG. 2 shows the stent after deployment. The stent consists of a metal lattice I with interstices 2. In use, a conventional balloon angioplasty procedure is often first performed to create a larger lumen in an occluded vessel, illustrated in FIG. 3A showing plaque 3 inside a coronary artery 4. Then, using a second balloon, the stent can be expanded at the site of the occlusion to a diameter slightly larger than the normal inner diameter of the vessel. The metal lattice 1 holds the compressed plaque against the vessel wall, as shown in FIG. 3B. If therapeutic agents are present coating the stent 1, the agents can pass into the vessel wall 4 on the right side, where there is little or no plaque, but agent penetration may be inhibited by the plaque 3 built up on the left side of the artery. The thickness of residual plaque in patients with coronary artery disease following angioplasty and stent placement may be in the range from 100 to 200 μm thick. In order to prevent restenosis, genes or drugs placed on the surface of a stent may benefit from a mechanism to penetrate the layer of compressed plaque barrier to gain entry to the vessel wall, particularly through the internal elastic lamina into the media and/or adventitia where the biology of restenosis resides.

In an effort to overcome the above described shortcomings, methods and apparatuses for drug and gene delivery are provided by Reed et al. (U.S. Pat. No. 6,197,013), incorporated by reference herein for all purposes. The Reed et al. devices allow diffuse delivery of a drug or gene to the coronary artery. This is accomplished by arrays of micromechanical probes present on the surface of the devices which penetrate the plaque and allow for efficient transport of therapeutic agents into the artery wall, in some cases directly to the artery media. The direct injection of therapeutic agents through the atherosclerotic plaque into the artery wall enables a wider variety of pharmaceuticals to be used when compared to the drugs used in current drug eluting stents. The probes can be part of a coronary stent which remains in the artery, or can be part of the angioplasty balloon, which is removed after the interventional procedure. The Reed et al devices differ from conventional methods in that a direct physical penetration of vascular plaque is accomplished.

While the Reed et al. devices represents a significant advancement, still further improvements would be desirable. The drug delivering probes of the Reed et al. devices preferably extend between 25 microns and 1000 microns from a surface of a deployment mechanism, such as a vascular stent, angioplasty balloon or an electrophoretic device. In most embodiments, particularly those including vascular stents, the probes extend this distance from the surface in the undeployed position. Deployment of the deployment mechanism involves radial force that pushes the probes such that they penetrate the vessel wall. The deployment mechanism preferably includes a removable housing, such as a sheath, in which the probes are disposed when the housing is in a closed state but is separate from the probes when the probes are deployed. This housing structure and the enclosed probes increase the minimum size of the deployment mechanism and possibly the risk of trauma to the vessel wall. Further, the designs of the Reed et al. devices suggest silicon micromachining techniques to produce the probes rather than conventional laser machining. It would be desirable to provide systems and devices having a lower profile for introduction to the blood vessel or body lumen. This would reduce the overall size of the device and possibly reduce the risk of trauma upon introduction to the vessel. Further it would be desirable to provide devices which may be produced by conventional laser machining.

In addition, it would be desirable to provide systems and devices which would secure the device in place and provide a mechanical seal to the vessel wall. One drawback of many conventional stents is the tendency of such stents to migrate downstream from the initial placement area. For example, due to irregularity in the vessel diameter or underexpansion of the stent, such stents have been observed to migrate downstream from the initial placement area. Thus, not only is the objective of the stent implantation not achieved, but the migrating stent may cause injury elsewhere in the vascular system. Further, a problem associated with grafts used for endovascular repair, particularly of aneurysms, is postprocedural leakage around the graft. Often, when leakage occurs, blood fills the aneurysmal sac due to gaps forming between the graft and the inner wall of the vessel. When vascular grafts fail due to leakage, the patient's condition is often compromised. Thus, it would be advantageous to provide systems and devices which reduce the risk of leakage. At least some of these objectives will be achieved by the inventions described hereinafter.

BRIEF SUMMARY OF THE INVENTION

The present invention provides apparatuses, systems and methods for treating a patient by positioning an expandable body having one or more microstructures within a body lumen and penetrating the lumen wall with the microstructures. The microstructures are formed in or attached to the expandable body in a low profile fashion suitable for atraumatic introduction to the body lumen with the use of a catheter or other suitable device. Each microstructure has an end which is attached to the expandable body and a free end. Once the apparatus is positioned within the body lumen in a desired location, the body is expanded and the microstructures deploy to a position wherein the free ends project radially outwardly. The free ends of the deployed microstructures then penetrate the lumen wall by continued expansion of the body. Additionally, a therapeutic agent may be delivered to the lumen wall by the microstructures. When the expandable body comprises a stent, the mechanism may be left in place, the microstructures providing anchoring and sealing against the lumen wall. When the body comprises a portion of an instrument, the expandable body may be retracted after delivery of the therapeutic agent and removed.

According to a first aspect of the present invention, an apparatus is provided comprising an expandable body having a proximal end, a distal end, and a longitudinal axis. The apparatus further includes at least one microstructure having an attached end attached to the body and a free end. The at least one microstructure is moveable from an undeployed position to a deployed position wherein the free end projects radially outwardly from the longitudinal axis. In the undeployed position, the microstructures are typically substantially aligned with an outer surface or perimeter of the body. However, it may be appreciated that the microstructures may lie beneath the surface, just so as the free ends do not project substantially outward beyond the surface.

Typically, the at least one microstructure has a directional axis between the free end and the attached end. The directional axis of each microstructure may extend in any direction. For example, each microstructure may be arranged so that its directional axis extends along the longitudinal axis, such as in a parallel manner. Alternatively, each microstructure may be arranged so that its directional axis extends across the longitudinal axis at an angle, such as in a perpendicular manner. Thus, the microstructures may be deployed to project radially outwardly regardless of their arrangement and orientation of their directional axes. Although the deployed microstructures may extend radially any distance from the expandable body, a distance of between 25 µm and 5000 µm is preferred.

In preferred embodiments, the expandable body comprises a series of interconnected solid sections having spaces therebetween, such as resembling a conventional vascular stent. However, in contrast to conventional stents, the at least one microstructure is formed by at least one of the solid sections. In some embodiments, expansion of the body creates forces within the body causing mechanical deformation of the solid sections. This in turn deploys the microstructures. Since the apparatus relies upon the utilization of such mechanical deformation of the body to deploy the microstructures, additional processing beyond conventional laser machining is not necessary to create the microstructures.

In some embodiments, each microstructure has first and second supports and a free end, the supports affixed to associated first and second adjacent portions of the radially expandable body. Expansion of the expandable body within the patient effects relative movement between the associated first and second portions of the expandable body, the relative movement deploying the microstructures.

The expandable body can have any shape including a cylindrical shape similar to the overall shape of conventional stents. These shapes, particularly cylindrical shapes, have a circumference. Thus, relative movement of the associated first and second portions of the expandable body may comprise circumferential movement of the first portion relative to the second portion. Although the associated first and second portions may move circumferentially as the body expands, the portions may or may not be circumferentially aligned. In some embodiments wherein the associated first and second portions are in circumferential alignment, the circumferential movement of the first portion relative to the second portion draws the free end toward the circumferential alignment. In some of these and other embodiments, the circumferential movement pulls the affixed ends of the first and second supports apart which moves the free end. When the expandable body includes an interior lumen (such as a stent) configured for receiving an expandable member(such as a balloon catheter) movement of the free end may create friction against the expandable member as the expandable member expands the expandable body, the friction projecting the free end radially outwardly.

In some preferred embodiments, the first and second supports comprise elongate shafts extending between the free end and the associated first and second adjacent portions of the radially expandable body. The relative movement of the associated first and second portions of the expandable may comprise moving the associated first and second portions apart so that the supports pull the free end in opposite directions causing the free end to project radially outwardly. Often the elongate shafts are adjacent to each other and aligned with a circumference of the expandable body in the undeployed position. Thus, expansion of the body maintains the adjacent positioning of the shafts but moves them apart.

In some preferred embodiments, each microstructure further includes a third support affixed to an associated third potion of the radially expandable body, the associated first and third portions being connected so as to move in unison. Often, the first, second and third supports comprise elongate shafts attached to the free end and the associated first, second and third adjacent portions of the radially expandable body, respectively. Typically, the second support is disposed longitudinally between the first and third supports. Thus, the relative movement of the associated first and second portions of the expandable body can move the associated first and second portions apart while the associated third portion moves in unison with the associated portion so that the supports pull the free end in opposite directions forming a tripod structure which projects the free end radially outwardly.

In other preferred embodiments, the expandable body has an inner ring and an outer ring surrounding a longitudinal axis. The rings form a lumen having a cross-sectional diameter. In addition, at least one microstructure is included, each microstructure having a first support, a second support and a free end. The first support is affixed to the inner ring and the second support is affixed to the outer ring. Expansion of the expandable body effects relative movement between the inner ring and outer ring which deploy the microstructures.

And, in still other preferred embodiments, the expandable body having an inner lumen and at least one microstructure having an attached end, a free end and a protruding region between the attached end and the free end. The protruding region may take any form or shape, such as forming an angle between the attached end and the free end. Typically, the microstructures are deployable by applying force to the protruding region from within the inner lumen. Depending on the shape of the protruding region, such force may be applied in a variety of directions to achieve deployment of the microstructures.

In a second aspect of the present invention, a material is provided which is carried by the at least one microstructure, wherein the material is delivered to the patient upon deployment of the apparatus. The material may include drugs, RNA, DNA, genes, genes encoding for nitric oxide synthase or vascular endothelial growth factor, prednisone, low molecular weight heparin or low molecular weight hirudin, Rapamycin/Sirolimus, Paclitaxel, Tacrolimus, Everolimus, Tyrphostin AG 1295, CGS-21680 Hydrochloride, AM 80, Estradiol, Anti-sense compounds, E2F Decoys (see Nakamura, T. et al. "Molecular strategy using cis-element 'decoy' of E2F binding site inhibits neointimal formation in porcine balloon-injured coronary artery model", in Gene Therapy (2002) 9, 488-494), incorporated herein by reference for all purposes), other therapeutic agents to be delivered to the lumen wall for therapeutic purposes, or any combination of these.

The material may be carried by the at least one microstructure in a variety of ways. For example, the material may be coated on a surface of the at least one microstructure or held in a lumen within the at least one microstructure. When the material comprises DNA, the microstructures may be coated with an adhesive material to which DNA adheres, such as gold. The material may also be coated with a hydrogel polymer or biocompatible material which provides a protective coating to the drugs and/or DNA. Alternatively, the material may be housed in a porous coating deposited onto and/or etched into the surface of the microstructures.

As mentioned, the expandable body may comprise an endoluminal stent. Typically, the stent is sized for positioning within a vascular lumen, however it may be appreciated that the stent may be sized for positioning within a variety of other body lumens. Expansion of the body may be achieved by any suitable means, such as by expansion of an expandable member, such as an inflatable member or balloon, particularly an angioplasty balloon, within the body or by self-expansion. Typically the bodies are comprised of stainless steel, titanium, tantalum, vanadium, cobalt chromium alloys, polymers, or shape-memory alloys, such as nickel-titanium alloys, which are particularly suitable for self-expansion. The body may be configured to maintain the deployed position and remain in the lumen, such as to function as a stent, or may be retracted to the undeployed position for removal.

In a third aspect of the present invention, methods are provided for treating a patient with the use of an expandable body having a proximal end, a distal end, a longitudinal axis therebetween, and at least one microstructure having an end attached to the body and a free end. In one embodiment, the expandable body is positioned in an undeployed position within a vessel of the patient. The body is then expanded to a deployed position within the vessel which projects the free end of the microstructure radially outward from the longitudinal axis and penetrates a wall of the vessel.

In vascular vessels, the wall of the vessel comprises an intimal layer, a medial layer and an adventitial layer. Expansion of the body may allow penetration of the free end through at least the intimal layer. In addition, expansion the body can penetrate the free end through at least the medial layer. As previously mentioned, expanding the body may comprise inflating an inflatable member within the mechanism so as to increase its cross-sectional diameter. Alternatively, the body can be self-expanding and expanding the body comprises releasing the body to allow self-expansion.

In some embodiments, the at least one microstructure carries a material, the method of the present invention further comprising delivering the material to the patient. When the material is coated on a surface of the at least one microstructure, delivering the material comprises transferring the material from the surface of the at least one microstructure to the penetrated vessel wall. When the material is held in a lumen within the at least one microstructure, delivering the material comprises injecting or somehow allowing the material to enter into the penetrated vessel wall.

Other objects and advantages of the present invention will become apparent from the detailed description to follow, together with the accompanying drawings.

BRIEF DESCRIPTION OF THE DRAWINGS

FIG. 4 is a perspective view of an embodiment of an apparatus of the present invention comprising an expandable body and at least one microstructure.

FIGS. 5A-5B provide cross-sectional views of the apparatus of FIG. 4 in the unexpanded and expanded states, respectively.

FIG. 5C illustrates an embodiment having microstructures extending along the length of the body in a substantially uniform pattern.

FIG. 5D illustrates an embodiments having microstructures present near the proximal and distal ends.

FIG. 5E illustrates two separate apparatuses partially inserted within one another or overlapped.

FIGS. 5F-5G illustrate embodiments of apparatus in a curved configuration.

FIGS. 6A-6B, 7A-7B illustrate possible relationships of the directional axis of the microstructure to the longitudinal axis of the body.

FIG. 8 illustrates an embodiment of the apparatus wherein the microstructures are aligned as in FIGS. 6A-6B, and FIG. 8A provides an exploded view of a microstructure of FIG. 8.

FIGS. 9A-9B shows the microstructure of FIG. 8A in an undeployed and deployed position, respectively.

FIGS. 11A-11C illustrate an additional embodiment of the microstructures.

FIG. 12 illustrates an embodiment of the apparatus wherein the microstructures are aligned as in FIGS. 7A-7B, and FIG. 12A provides an exploded view of a microstructure of FIG. 12.

FIG. 13A illustrates circumferential movement of associated first and second portions when the portions are circumferentially aligned while FIG. 13B illustrates circumferential movement of the portions when the portions are not circumferentially aligned.

FIGS. 15A-15C illustrate embodiments of the free ends of the microstructures of FIG. 12A.

FIGS. 15D-15G illustrate embodiments of the apparatus having various designs.

FIG. 15H illustrates the embodiment depicted in FIG. 15G having the microstructures in a deployed position.

FIG. 15I provides a schematic cross sectional view of FIG. 15H.

FIGS. 16A-16C illustrate an embodiment including inner and outer rings, relative movement between which deploy the microstructures.

FIGS. 17A-17C illustrate an additional embodiment of the present invention wherein expansion of the expandable member and deployment of the microstructures may be achieved independently.

FIGS. 18-18A illustrate embodiments of the apparatus including internal lumens for delivery of therapeutic material.

FIG. 19 illustrates a cross-sectional view of the expandable body expanded inside a blood vessel lumen, and FIG. 19A provides an exploded view of a microstructure penetrating the wall of the vessel lumen.

DETAILED DESCRIPTION OF THE INVENTION

Figure 1:
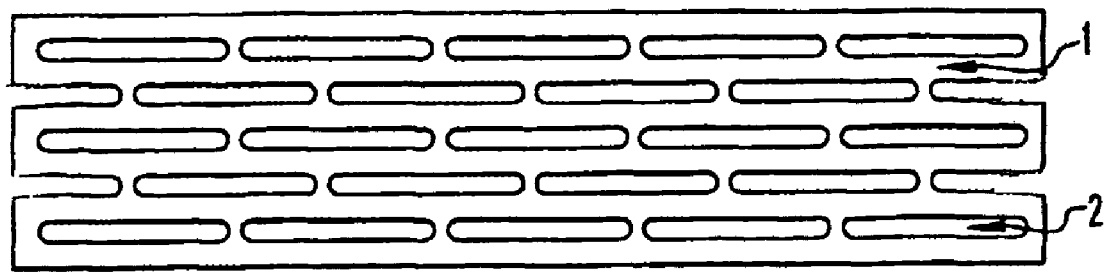
FIGS. 1-2 show an ordinary stent before expansion and after deployment, respectively.
Figure 2:
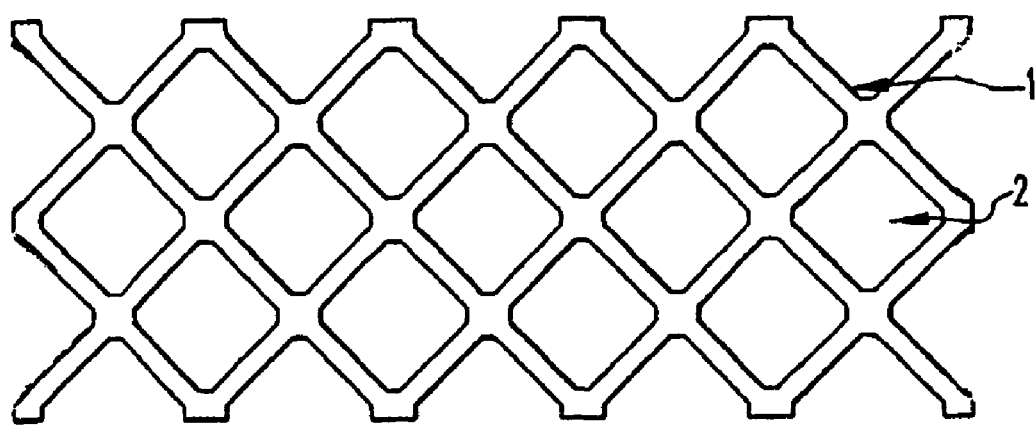
Figure 3A:
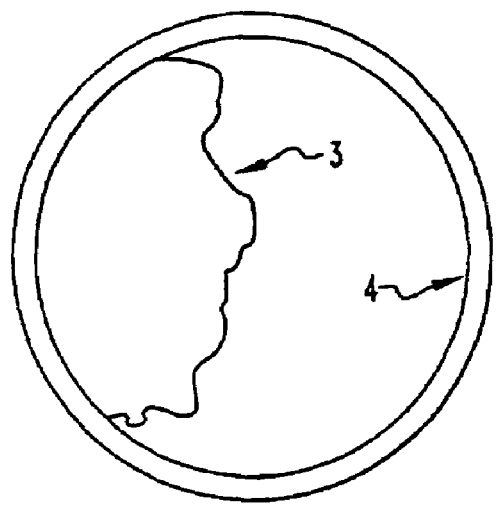
FIGS. 3A-3B show plaque build-up inside a coronary artery, and after conventional balloon angioplasty and stenting, respectively.
Figure 3B:
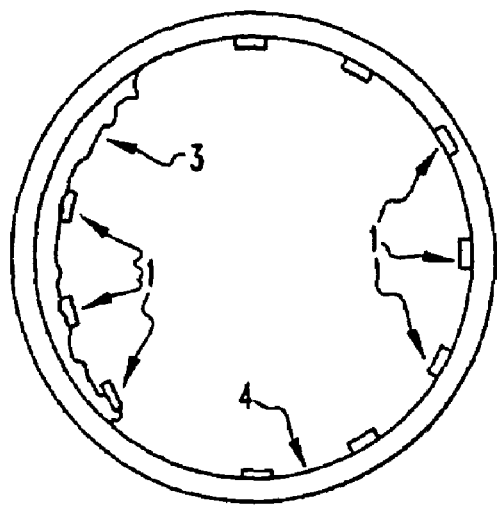

The following detailed description illustrates the invention by way of example, not by way of limitation of the principles of the invention. Referring to FIG. 4, an embodiment of an apparatus 10 of the present invention is illustrated, the apparatus 10 comprises an expandable body 12 and at least one microstructure 14. The expandable body 12 has a proximal end 16, a distal end 18, a longitudinal axis 20 therebetween. A cross-sectional diameter 24 is also shown. In this embodiment, the expandable body 12 comprises a cylindrical structure surrounding the longitudinal axis 20. However, it may be appreciated that the expandable body 12 can comprise any shaped structure, including oval, hemispherical, ellipsoidal, spherical, square, rectangular, or polygonal, to name a few, and may be symmetrical or non-symmetrical. Further, the expandable body 12 may be sized and shaped for delivery from a catheter or other suitable device for positioning within a body lumen. The embodiment of FIG. 4 is suitable for permanent placement within the body lumen, such as to resemble a conventional vascular stent. However, it may be appreciated that the expandable body 12 may be formed as a portion of an instrument which is used to treat a body lumen and is then removed. For example, the expandable body 12 may be expanded within a body lumen to deploy the microstructures, the wall of the lumen penetrated by the microstructures and treated by delivery of drugs or other material from the microstructures to the lumen wall, and the expandable body 12 then retracted and removed.

Together, the microstructures 14 and the expandable body 12 form the cylindrical structure surrounding the longitudinal axis 20. FIG. 4 illustrates the apparatus 10 in an unexpanded state wherein the microstructures 14 are in an undeployed position. Here, the microstructures 14 are preferably aligned or flush with an outer surface 22 of body 12 so that the surface 22 does not include substantial protrusions. Alternatively, the microstructures 14 may be positioned below the surface 22.

FIGS. 5A-5B provide cross-sectional views of the apparatus 10 of FIG. 4 in the unexpanded and expanded states, respectively. FIG. 5A shows the wall of the body 12 within which lie microstructures 14, highlighted by shading. Thus, when the expandable body 12 is in the unexpanded state, the microstructures 14 are in an undeployed position which is aligned with the surface 22. FIG. 5B illustrates the expandable body 12 in an expanded state wherein the cross-sectional diameter 24 is increased. Here, the microstructures 14 are in a deployed position wherein a free end 32 of each microstructure 14 projects radially outward from the longitudinal axis 20 while an attached end 30 remains attached to the body 12. As will be described later, in some embodiments the mechanical act of expansion of the body 12 creates forces which deploy the microstructures 14. It may be appreciated that the deployed microstructures 14 may form any angle with the surface 22, including a substantially 90 degree angle as shown. Further, different microstructures 14 may form different angles, angles may vary randomly or in a pattern, angles may be selectable particularly based on amount of expansion, and some microstructures may not deploy while others deploy.

It may be appreciated that any number of microstructures 14 may be present and may be arranged in a variety of patterns along the entire length of the body 12 or along any subportion. Referring to FIG. 5C, an embodiment is illustrated having microstructures 14 extending along the length of the body 12 in a substantially uniform pattern. The microstructures 14 are illustrated in deployed positions for ease of identification and visualization. Alternatively, for example, microstructures 14 may be present along one side of the expandable body 12 and not the other. Or, as illustrated in FIG. 5D, microstructures 14 may be present near the proximal end 16 and distal end 18 and not therebetween. Likewise, microstructures 14 may only be present near one of the ends 16, 18. This may be particularly useful in delivery of therapeutic agents to the peri-vascular or peri-adventitial areas of blood vessels where such agents are more mobile and less dependent on multiple delivery locations. Referring now to FIG. 5E, two separate apparatuses 10 are shown partially inserted within one another or overlapped. By arranging the microstructures 14 near the ends 16, 18, the overlapping of the expandable bodies 12 does not result in overlapping of microstructures 14. This ensures that no portion of the apparatus 10 or overlapped apparatuses will contain more than a single layer of microstructures 14. However, it may be appreciated that any number of apparatuses 10 with any arrangement of microstructures 14 may be used, particularly if an abundance of microstructures 14 are desired to be present.

Although the previous embodiments have been illustrated in a straight or linear configuration, the apparatuses 10 of the present invention may be positioned in a variety of curved, angled or twisted configurations when placed within body lumens. Body lumens, particularly blood lumens or the vasculature, include segments which are non-linear. FIGS. 5F-5G illustrate embodiments of apparatus 10 in a curved configuration. When microstructures 14 are present along a midsection of the expandable body 12, as shown in FIG. 5F, the curvature of the body 12 directs the microstructures 14 along inner arc 15 to concentrate in a small area This may be desirable for targeting a specific area with therapeutic agents. However, if such concentration is not desired, microstructures 14 may alternatively be arranged near the ends 16, 18 so that microstructures 14 along inner arc 15 are not concentrated, as shown in FIG. 5G. It may be appreciated that the microstructures 14 may alternatively be arranged near end 16 only, near end 18 only or along any portion of the apparatus 10.

Any spacing between the microstructures 14 may also be used, preferably between 5 microns and 10,000 microns. Deployed microstructures have heights which may vary but are typically sufficient to penetrate the lumen wall to a desired depth. This may require traversal of the thickness of the compressed plaque. Thus, the deployed microstructures may have heights which vary from less than 25 μm to over 5000 μM.

As illustrated in FIG. 4, the expandable body 12 may comprise a series of interconnected solid sections 36 having spaces 35 therebetween. In preferred embodiments, the expandable body 12 comprises an endoluminal stent. Although such stents may be introduced into various body lumens, such as within the lungs, gastrointestinal tract, urethra, or ureter, to name a few, stents are commonly used in the vascular system, particularly the coronary arteries. Conventional vascular stents are typically formed from wires bent or woven to define a series of relatively tightly spaced convolutions or bends or from a solid metal structure from which portions are removed in a selected pattern. The expandable body 12 of the present invention may resemble conventional stents and may be similarly manufactured, however the particular design of the structure is dependent upon the microstructures and the way that they deploy upon expansion of the body 12. Examples of such designs will be provided in later sections. Thus, special processing is not necessary for the fabrication of the devices of the present invention. For example, the expandable body 12 can be laser machined from annealed 316L tubing; electric discharge machining (EDM) or electrochemical etching can also be used to fabricate the devices, to name a few.

As mentioned, each microstructure 14 has an attached end 30, attached to the body 12, and a free end 32, both in the deployed and undeployed positions. In preferred embodiments, each microstructure has a directional axis 40, such as shown in FIG. 6A, between the free end 32 and the attached end 30. In some embodiments of the apparatus 10, the directional axis 40 extends across the longitudinal axis 20 at an angle while the microstructure 14 is in the undeployed position. Here, the directional axis 40 is shown to form an angle of approximately 90 degrees with the longitudinal axis 20. Deployment of the microstructure 14 projects the free end 32 radially outwardly from the longitudinal axis 20, as shown in FIG. 6B, so that the microstructure 14 extends beyond the surface 22. Alternatively, in some embodiments, the directional axis 40 extends along the longitudinal axis 20 while the microstructure 14 is in the undeployed position, as illustrated in FIG. 7A. In this case, deployment of the microstructure 14 also projects the free end 32 radially outward from the longitudinal axis 20, as shown in FIG. 7B, so that the microstructure 14 extends beyond the surface 22.

Generally, the expandable body 12 comprises a series of interconnected solid sections having spaces therebetween. The solid sections form the structure of the expandable body 12 and form the microstructures 14. In most embodiments, each microstructure has at least a first support and a second support and a free end, the first and second supports being affixed to associate first and second adjacent portions of the radially expandable body. Expansion of the expandable body effects relative movement between the associated first and second portions of the expandable body. For example, the relative movement of the associated first and second portions of the expandable body may comprise circumferential movement of the first portion relative to the second portion when the expandable body expands radially. Although this relative movement may be in any direction, typically the relative movement comprises moving the associated first and second portions apart. Often the circumferential movement pulls the affixed ends of the first and second supports apart, which in turn moves the free end. Thus, such relative movement deploys the microstructures from an undeployed position along the expandable body to a deployed position with the free end projecting radially outwardly from the longitudinal axis. A variety of embodiments are provided to illustrate these aspects of the present invention.

FIG. 8 illustrates an embodiment of the apparatus 10 wherein the microstructures 14 are oriented as in FIGS. 6A-6B. Thus, although the apparatus 10 is illustrated in a flat plane, it is formed cylindrically around longitudinal axis 20 in this embodiment. As shown, the body 12 comprises a series of interconnected solid sections 36 having spaces 35 therebetween. A portion of the apparatus 10 including a microstructure 14 is illustrated in exploded view in FIG. 8A. Here, a first support 37a, a second support 37b and a third support 37c are shown, each comprising elongate shafts, wherein the second support 37b is disposed longitudinally between the first support 37a and third support 37c. The first, second, and third supports 37a, 37b, 37c are attached to the free end 32 and to first, second and third adjacent portions 38a, 38b, 38c, respectively, of the expandable body, as shown. FIG. 9A shows the microstructure 14 of FIG. 8A wherein the supports 37a, 37b, 37c are adjacent to each other and aligned with a circumference 39 of the expandable body 12 in the undeployed position. Here, the body 12 is in the unexpanded state, wherein the cross-sectional diameter has a radius $R_1$. FIG. 9B shows the body 12 is in the expanded state, wherein the cross-sectional diameter has a larger radius $R_2$. Such expansion draws the first and second associated portions 38a, 38b, apart while the associated third portion 38c moves in unison with the associated first portion 38a. Thus, the supports 38a, 38b, 38c pull the free end in opposite directions forming a tripod structure which causes the free end to project radially outwardly, as shown.

Figure 10A:
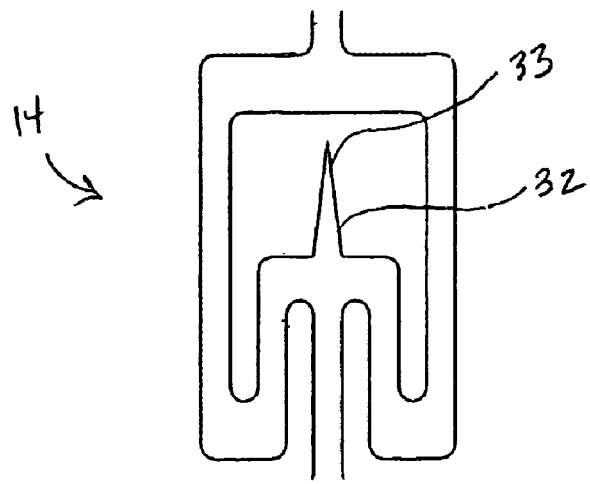
FIGS. 10A-10C illustrate embodiments of the free ends of the microstructures of FIG. 8A.
Figure 10B:
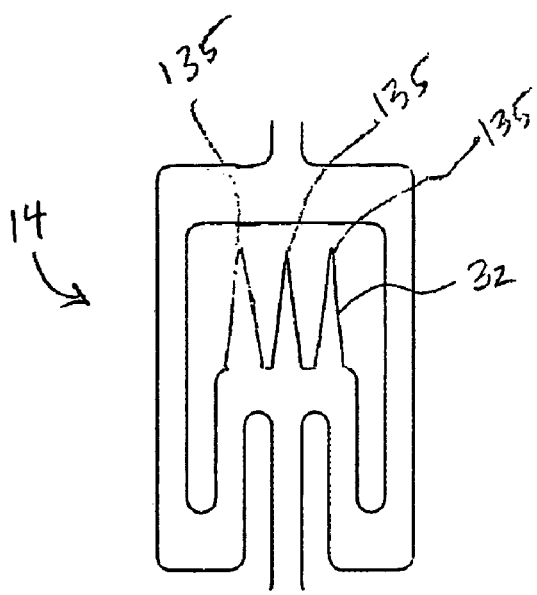
Figure 10C:
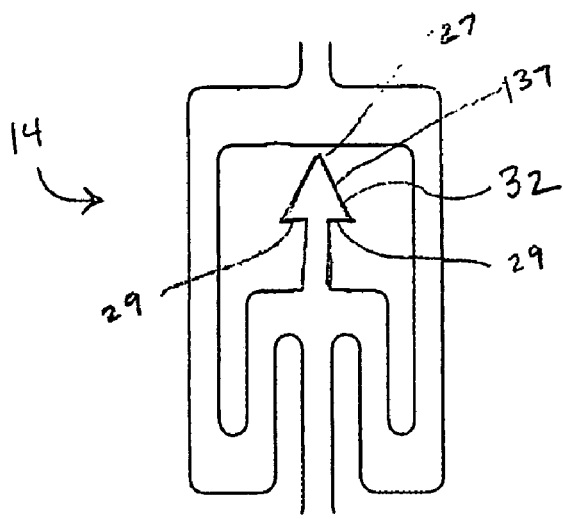

The free ends 32 of the microstructures 14 depicted in FIG. 8 and FIG. 8A are each shown to have a flat-edged shape. However, the free ends 32 may have any desired shape. For example, FIGS. 10A-10C illustrate additional embodiments of microstructures 14 having different shaped free ends 32. In each of these embodiments, the free ends 32 have a pointed shape. When the apparatus 10 is positioned in a body lumen, such as a blood vessel, the pointed shapes of the free ends 32 may assist in penetration of the lumen wall. The shape, size and tapering of each point may possibly guide the free end 32 to a certain penetration depth, such as to a specified tissue layer. In FIG. 10A, the free end 32 has a single point 33 and in FIG. 10B the free end 32 has multiple points 135. In FIG. 10C, the free end 32 has an arrow-shaped point 137. The arrow-shaped point 137 includes a pointed tip 27 and at least one undercut 29 to reduce the ability of the free end 32 from withdrawing from a lumen wall once penetrated. This may be useful when the microstructures are used for anchoring. It may be appreciated that microstructures 14 throughout the apparatus 10 may all have the same free end 32 shape or the shapes may vary randomly or systematically.

FIG. 11A also illustrates an embodiment of the apparatus 10 wherein the microstructures 14 are oriented as in FIGS. 6A-6B. FIG. 11A provides a portion of the apparatus 10 including the microstructure 14 in exploded view. In this embodiment, the microstructure 14 has first and second supports 37a, 37b and a free end 32, the supports 37a, 37b affixed to associate first and second adjacent portions 38a, 38b of the radially expandable body 12. FIG. 11B shows the microstructure 14 of FIG. 11A wherein the supports 37a, 37b are adjacent to each other and aligned with a circumference 39 of the expandable body 12 in the undeployed position. Here, the body 12 is in the unexpanded state, wherein the cross-sectional diameter has a radius $R_1$. The first and second supports 37a, 37b comprise elongate shafts extending between the free end 32 and the associated first and second adjacent portions 38a, 38b of the radially expandable body 12. FIG. 11C shows the body 12 is in the expanded state, wherein the cross-sectional diameter has a larger radius $R_2$. As shown, relative movement of the associated first and second portions 38a, 38b of the expandable body moves the associated first and second portions 38a, 38b apart so that the supports 37a, 37b pull the free end in opposite directions causing the free end 32 to project radially outwardly.

It may be appreciated that although the free end 32 is illustrated to have a pointed shape, the free ends 32 may have any desired shape, including the shapes illustrated in FIGS. 10A-10C. And, it may also be appreciated that microstructures 14 throughout the apparatus 10 may all have the same free end 32 shape or the shapes may vary randomly or systematically.

FIG. 12 illustrates an embodiment of the apparatus 10 wherein the microstructures 14 are oriented as in FIGS. 7A-7B. Thus, although the apparatus 10 is illustrated in a flat plane, it is formed cylindrically around longitudinal axis 20 in this embodiment. As shown, the expandable body 12 comprises a series of interconnected solid sections 36 having spaces 35 therebetween. A portion of the body 12 including a microstructure 14 is illustrated in exploded view in FIG. 12A. Each microstructure has a first support 37a, a second support 37b and a free end 32. The supports 37a, 37b are affixed to associate first and second adjacent portions 38a, 38b of the radially expandable body.

Referring to FIG. 13A, the associated first and second portions 38a, 38b may be in circumferential alignment, as illustrated by dashed line 41. It may be appreciated that dashed line 41 wraps around to form a circular shape when following the circumference of a cylindrical body, however the dashed line 41 is illustrated as a straight line for clarity. When the expandable body expands radially, the relative movement of the associated first and second portions 38a, 38bmay comprise circumferential movement of the first portion 38a relative to the second portion 38b, as indicated by arrows 42. When the associated first and second portions 38a, 38b may be in circumferential alignment, as shown, the circumferential movement of the first portion 38a relative to the second portion 38b draws the free end 32 toward the circumferential alignment or line 41, as indicated by arrow 44.

Referring to FIG. 13B, the associated first and second portions 38a, 38b may be in noncircumferential alignment, as illustrated by dashed line 46 which forms an angle with line 41 representing circumferential alignment. Thus, when the expandable body expands radially, the relative movement of the associated first and second portions 38a, 38bmay still comprise circumferential movement of the first portion 38a relative to the second portion 38b, as indicated by arrows 42. And, the circumferential movement of the first portion 38a relative to the second portion 38b pulls the affixed ends of the first and second supports 37a, 37b apart which moves the free end 32. However, in this situation, the free end is no longer drawn toward the circumferential alignment, rather the free end is drawn toward line 46 as indicated by arrow 48.

Figure 14A:
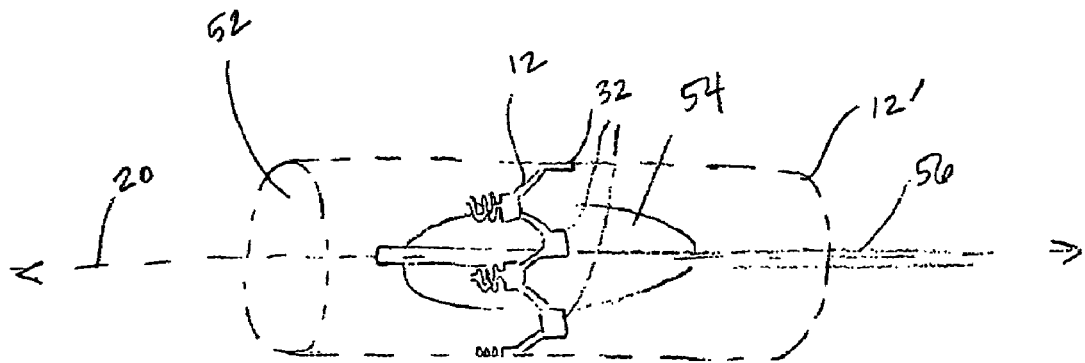
FIG. 14A illustrates a representative portion of the radially expandable body having a cylindrical shape and FIGS. 14B-14C illustrate the movement of the expandable body, particularly the movement of the free ends of the microstructures as the expandable member radially expands the body.
Figure 14B:
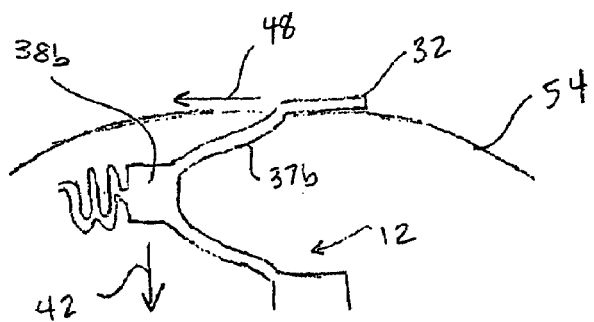
Figure 14C:
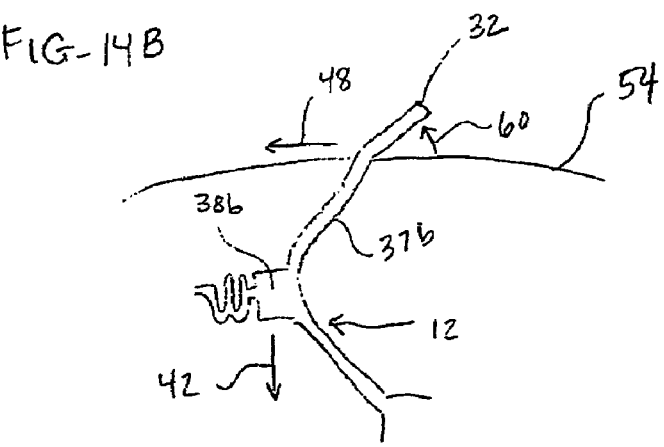

FIG. 14A illustrates a representative portion of the radially expandable body 12 having a cylindrical shape, the remainder of the body illustrated by dashed body 12'. In this embodiment the radially expandable body 12 further comprises an interior lumen 52 along the longitudinal axis 20. The interior lumen 52 may be configured for receiving an expandable member 54 which expands the expandable body 12, as illustrated. In this case, the expandable member 54 is typically mounted on a catheter 56. FIGS. 14B-14C illustrate the movement of the expandable body, particularly the movement of the free ends 32 of the microstructures 14 as the expandable member 54 radially expands the body 12. FIG. 14B is a side view of a portion of the expandable body 12, including a microstructure 14, mounted on expandable member 54. Expansion of the expandable member 54 effects relative movement between the associated first and second portions 38a, 38b, in this case such expansion effects circumferential movement. Circumferential movement is indicated by arrow 42. It may be appreciated that the associated first portion 38a is not shown in FIG. 14B since FIG. 14B is a side view and portion 38a would be located symmetrically on the backside of the expandable member 54. The circumferential movement pulls the affixed ends of the first and second supports 37a, 37b apart which moves the free end 32, indicated by arrow 48. As shown in FIG. 14C, such movement of the free end 32 projects the free end 32 radially outwardly, as indicated by arrow 60. Such projection may be due to torsional deformation of the first and second supports 37a, 37b, caused by the increased separation between the associated first and second portions 38a, 38b resulting from expansion of the expandable body 12. Such projection may also be due to friction created between the free end 32 and the expandable member 54 as the expandable member 54 expands the expandable body 12. Alternatively, such projection may be due to other factors, such as the direction of movement of the supports 37a, 37b, the shape of the supports 37a, 37b, or a combination of factors.

It may be appreciated that the expandable body 12 of FIGS. 14A-14C may alternatively be expanded by means other than expansion by an expandable member 54. For example, the expandable body 12 may be self-expanding, as previously mentioned. In this situation, the expandable body 12 is preformed so that deployment of the body 12 allows the body 12 to self-expand toward a predetermined configuration. Preforming may be achieved with the use of an expandable member 54, wherein the body 12 is set while surrounding an expandable member 54 so as to later form this configuration. When the expandable body 12 expands within the body, projection of the microstructures may be due to torqueing or movement of the supports 37a, 37b, for example.

The free ends 32 of the microstructures 14 depicted in FIGS. 12, 12A, 13A-13B, 14A-14C are each shown to have a flat-edged shape. However, the free ends 32 may have any desired shape. For example, FIGS. 15A-15C illustrate additional embodiments of microstructures 14 having different shaped free ends 32. In each of these embodiments, the free ends 32 have a pointed shape. When the apparatus 10 is positioned in a body lumen, such as a blood vessel, the pointed shapes of the free ends 32 may assist in penetration of the lumen wall. The shape, size and tapering of each point may possibly guide the free end 32 to a certain penetration depth, such as to a specified tissue layer. In FIG. 15A, the free end 32 has a single point 33 and in FIG. 15B the free end 32 has multiple points 135. In FIG. 15C, the free end 32 has an arrow-shaped point 137. The arrow-shaped point 137 includes a pointed tip 27 and at least one undercut 29 to reduce the ability of the free end 32 from withdrawing from a lumen wall once penetrated. This may be useful when the microstructures are used for anchoring. It may be appreciated that microstructures 14 throughout the apparatus 10 may all have the same free end 32 shape or the shapes may vary randomly or systematically. Likewise, the free end 32 may have a flat-shaped inner edge 139, as illustrated in FIG. 15A, to maximize friction against an expandable member 54 or the free end 32 may have various other shaped inner edges 139, as illustrated in FIGS. 15B-15C.

FIGS. 15D-15F illustrate embodiments of the apparatus 10 having various designs. Again, although the apparatus 10 is illustrated in a flat plane, it is formed cylindrically around longitudinal axis 20 in each embodiment. In FIG. 15D, the microstructures 14 have free ends 32 which are shaped as a single point 33 and include a flat inner edge 139. Thus, the free ends 32 are similar to the embodiment illustrated in FIG. 15A. FIG. 15E also illustrates an embodiment wherein the microstructures 14 have free ends 32 which are shaped as a single point 33 and include a flat inner edge 139. However, in this embodiment, the microstructures 14 are positioned more closely together, in a denser pattern. In FIG. 15F the microstructures 14 have free ends 32 which are shaped to have multiple points 135 and to include a flat inner edge 139. In addition, the flat inner edge 139 is part of a flange 43 which is directed opposite of the points 135. The flange 43 provides a wide flat inner edge 139 to maximize friction against an expandable member 54 and a narrow neck region 45 to enhance flexibility and rotation of the multiple points 135 radially outwardly.

FIG. 15G illustrates an embodiment of the expandable body 12 wherein the free ends 32 of the microstructures 14 have a single point 33 and curved inner edge 139. And, FIG. 15H illustrates the microstructures of FIG. 15G in a deployed position. FIG. 15H provides a view similar to FIG. 14C wherein circumferential movement pulls the affixed ends of the first and second supports 37a, 37b apart which moves the free end 32. Such movement of the free end 32 projects the free end 32 radially outwardly, as indicated by arrow 60. As mentioned, such projection may be due to friction created between the free end 32 and the expandable member 54 as the expandable member 54 expands the expandable body 12.

Alternatively, such projection may be due to other factors, such as the direction of movement of the supports 37a, 37b, the shape of the supports 37a, 37b, or a combination of factors. For example, FIG. 15I provides a schematic cross sectional view of FIG. 15H. Prior to expansion, the free ends 32 and associated first and second portions 38a, 38b of the expandable member 12 lie substantially equidistant from the longitudinal axis 20. Upon expansion of the expandable member 54, the forces are applied to the first support 37a and second support 37b. Upon further inflation, the first and second supports 37a, 37b present less resistance to the expandable member 54, and as such the expandable member 54 expands more in the regions spanned by the first and second supports 37a, 37b than in the regions of the associated first and second portions 38a, 38b, as illustrated in FIG. 15I. This deploys the microstructures 14 since there is a contact point between the first and second supports 37a, 37b and the expandable member that serves as a fulcrum about which moment is generated as the expandable member continues to expand. The resulting moment further projects the microstructure radially outwardly.

FIGS. 16A-16C illustrate an additional embodiment of the present invention. FIG. 16A provides a cross-sectional view of an expandable body 12, the expandable body 12 having an inner ring 90 and an outer ring 92 surrounding the longitudinal axis 20. As shown, the rings 90, 92 form an lumen 94 having cross-sectional diameter 24. In addition, at least one microstructure 14 is included, each microstructure 14 having a first support 100, a second support 102 and a free end 104. The first support 100 is affixed to the inner ring 90 and the second support 102 is affixed to the outer ring 92.

Expansion of the expandable body 12 effects relative movement between the inner ring 90 and outer ring 92, as illustrated in FIG. 16B. Here, diverging lines 90', 92' correspond to diverging portions of inner ring 90 and outer ring 92, respectively. Since the first support 100 is affixed to the inner ring 90 and the second support 102 is affixed to the outer ring 92, the supports 100, 102 are drawn apart as the portions of the rings 90, 92 diverge. However, the supports 100, 102 are rotateably connected near the free end 104 at a connection point 108. This allows the microstructures to deploy or rotate as shown in FIG. 16B.

FIG. 16C illustrates the expandable body 12 of FIG. 16A in an expanded state wherein the microstructures 14 are deployed. As shown, cross-sectional diameter 12 has increased and the relative movement between the inner ring 90 and outer ring 92 has deployed the microstructures 14 from an undeployed position to a deployed position with the free end 104 projecting radially outwardly from the longitudinal axis 20.

Further, FIGS. 17A-17C illustrate an additional embodiment of the present invention. As shown in FIG. 17A, expandable body 12 has a proximal end 16, a distal end 18, a longitudinal axis 20 therebetween and at least one microstructure 14 having an attached end 30 and a free end 32 in an undeployed position. In addition, the expandable body 12 has an outer surface 110 which in this embodiment is the outer perimeter of the cylindrical expandable body 12. In the undeployed state, the attached end 30 and free end 32 are generally within the outer surface 110, either aligned with or below the outer surface 110. This allows the expandable body 12 to have a low profile in the unexpanded state so that it may be easily delivered to a body lumen without damage to the delivery device or lumen wall by protruding free ends 32.

Once positioned within the body lumen in a desired location, the microstructures 14 may then be deployed. In this embodiment, the expandable body 12 has an inner lumen 112 and each microstructure 14 has a protruding region 120 between the attached end 30 and the free end 32. The protruding region 120 may take any form or shape; here the protruding region 120 forms an angle between the attached end 30 and the free end 32. Typically, the microstructures 14 are deployable by applying force to the protruding region 120 from within the inner lumen 112. Depending on the shape of the protruding region 120, such force may be applied in a variety of directions to achieve deployment of the microstructures 14. For example, as shown in FIG. 17B, the microstructures 14 maybe deployed by applying force radially outwardly against the protruding region 120 as by expansion of an expandable member 130 within the inner lumen 112. Here, the expandable member 130 is shown mounted on a catheter shaft 134 and inserted through the inner lumen 112. The member 130 is expanded, in this case inflated, and the force applied to the protruding regions 120 rotates the free ends 32 radially outwardly from the longitudinal axis 20. In some embodiments, the attached ends 30 are attached to the expandable body 12 by rotateable joints, however it may be appreciated that the attached ends 30 may simply allow rotate of the free ends 32 by bending or mechanical deformation near the attached ends 30. Such mechanical deformation may be particularly suitable for maintaining deployment of the microstructures.

As shown in FIG. 17C, the expandable member 130 may then be removed and deployment of the microstructures 14 maintained. Deployment of the microstructures 14 may be maintained by the apparatus 10 itself, or it may be maintained by the surrounding lumen wall or plaque through which the microstructures may have penetrated. It may be appreciated that expansion of the expandable member 130 within the lumen 112 may have expanded the expandable body 12, in addition to deploying the microstructures 14. However, such expansion of the body 12 may be independent of deployment of the microstructures 14. Thus, the expandable body 12 be expanded once the microstructures 14 have deployed, as in FIG. 17C.

As mentioned, penetration of the lumen wall by one or more microstructures can be used to anchor the apparatus 10 within the lumen or to deliver drugs, genes or other therapeutic agents or material to or through the lumen wall. The material may be coated on a surface of the microstructures. When the material comprises DNA, each microstructure may be coated with an adhesive material to which DNA adheres, such as gold. Preferably, when the material comprises DNA, the material is a gene encoding for nitric oxide synthase or vascular endothelial growth factor. Nitric oxide synthase inhibits smooth muscle cells from growing and inhibits platelet and white blood cells adherence to denuded surfaces following coronary intervention. Vascular endothelial growth factor stimulates reendothelialization of an injured vessel. To increase the amount of drugs or genes held by the microstructures, the structural material could be made porous. A straightforward way of accomplishing this goal is to anodize the metal forming the apparatus or to coat the metal with a material which is then anodized. Anodization produces a high density of small, vertically oriented pores, of which the size and configuration can be controlled by varying the anodization current, temperature and solution concentration.

Further, the material may be coated with a biocompatible material which provides a protective coating to prevent the drug or gene from being washed away, and allows for the release of the drug and/or gene over a period of time. Such coatings include biodegradable materials, polymers, hydrogels, and porous ceramics. When the material is a drug which does not include DNA, the material is preferably Sirolimus or Paclitaxel. Sirolimus is a macrocyclic lactone with potent immunosuppressive effects. Sirolimus binds to an intracellular receptor protein and elevated p27 levels, which leads to the inhibition of cyclin/cyclin-dependent kinase complexes and, ultimately, induces cell-cycle arrest in the late G1phase. It inhibits the proliferation of both rat and human smooth muscle cells in vitro, and reduces intimal thickening in models of vascular injury. Paclitaxel is a taxoid which is used in chemotherapy. Paclitaxel binds to microtubules and inhibits their depolymerization into tubulin. This effectively stops the cells ability to breakdown the mitotic spindle during mitosis, preventing cell division and proliferation. Paclitaxel has also been shown to reduce intimal thickening in models of vascular injury.

Alternatively, as illustrated in FIGS. 18-18A, the material may be held in one or more internal lumens within the microstructures. FIG. 18 illustrates an embodiment of the apparatus 10 similar to the embodiment illustrated in FIG. 12. Here, the free ends 32 are shown to have pointed shapes. Each internal lumen 70 extends through a microstructure 14 to its free end 32. Thus, material within the lumen 70 is expelled from the free end 32 into the surrounding body lumen or tissue. The material can be actively pumped by a delivery microsystem or allowed to diffuse out of the lumen 70. Various types of delivery microsystems may be used, including electro-osmotic pumps, shape-memory transducers, expansion of polymer gels (such as water-absorbing polyacrylamid gel), osmotic pumps, piezo-electric actuators, electrostatic or electromagnetic pumps, or electro-dissolution of membranes (Santini, J. et al. "A controlled-release microchip", in Nature, Vol 397, Jan. 28, 1999, incorporated herein by reference for all purposes) to release the material followed by diffusion through lumen, to name a few. In the embodiment illustrated in FIG. 18A, the delivery microsystem includes a reservoir 72 within the associate first portion 38a of the expandable body 12 wherein lumen 70 extends through the first support 37a from the reservoir 72. The reservoir 72 may simply house the material, or the reservoir 72 may include a therapeutic delivery control device 74. This device 74 can be designed to release the material at predetermined intervals. The intervals may be based on pumping timing, controlled diffusion or triggering by an external signal. The external trigger may be in the form of a radiofrequency signal, an injectable chemical signal, such as an enzyme, or an ultrasonic signal, to name a few. Alternatively or in addition, cells (transplant or xenograft) may be encapsulated in an immuno-isolated device in the reservoir 72. This would allow cellular factories to be implanted that could be fed on the intraluminal side by nutrients, oxygen, etc., in the blood supply. Thus, the reservoir 72 may include a filter which allows contact with the blood supply. Therapeutic material generated by the cells may then be delivered to the vessel wall, particularly the adventitia Additionally, this system can work in reverse, with the device lumen serving as a conduit for nutrients from the adventitia into the vessel.

As mentioned previously, the present invention may be utilized for any sort of treatment which involves delivery of a therapeutic agent and/or anchoring of a device. The devices could be introduced into various body lumens, such as the vascular system, lungs, gastro-intestinal tract, urethra or ureter. The function of the microstructures includes but is not limited to facilitating drug and gene delivery, securing the device in place and providing a mechanical seal to the lumen wall.

Positioning of the apparatus of the present invention is typically performed via standard catheterization techniques. These methods are well known to cardiac physicians and are described in detail in many standard references. Examples of such positioning will be provided in relation to the vascular system, however, such example is not intended to limit the scope of the invention. In brief, percutaneous access of the femoral or brachial arteries is obtained with standard needles, guide wires, sheaths, and catheters. After engagement of the coronary arteries with a hollow guiding catheter, a wire is passed across the coronary stenosis where the apparatus is to be deployed. The apparatus is then passed over this wire, using standard coronary interventional techniques, to the site of atherosclerotic coronary plaque where drug and/or gene therapy is to be delivered.

The apparatus is then delivered and expanded to force the microstructures 14 through the atherosclerotic plaque, so the microstructure tips reach the vessel wall, as shown in FIGS. 19-19A. FIG. 19 shows a cross-sectional view of the expandable body 12 expanded inside a blood vessel lumen L. Microstructures 14 pierce through the layer of compressed plaque 3 and into the wall of the lumen L. FIG. 19A provides an exploded view of a microstructure 14 penetrating the wall of the lumen L. Here, an intimal layer L medial layer M and adventitial layer A are shown. The microstructure 14 may penetrate any or all of the layers I, M, A, including penetrating through the wall of the lumen L to the peri-adventitial space. FIG. 19A illustrates penetration to the adventitial layer A. Penetration allows for more efficient transfer of therapeutic material into the blood vessel wall, and, when desired, into the adventitial layer A. When delivering certain therapeutic materials, application from the endovascular space has lead to localization in the intima and inner media. This may be due to physical forces that augment drug transport through the arterial wall, for example, in the presence of convective forces that arise from physiological transmural pressure gradients. However, such delivery may not be sufficient for localizing therapeutic material in the adventitial layer. Perivascular release has led to the highest concentrations within the adventitial layer [Creel, C. et al. "Arterial Paclitaxel Distribution and Deposition" in Circulation Research, 2000;86:879-884]. Thus, in some cases it may be desired to penetrate the microstructures through to the peri-adventitial space. The therapeutic material which coats or is held within the microstructures then enters the lumen wall or is deposited peri-vascularly where it performs its desired biological function. If the apparatus is intended to function in a stent-like manner, the apparatus is then left behind in its expanded state. Alternatively, if the apparatus is simply intended for delivery of an agent, the apparatus may be retracted and removed.

Although the invention has been described in detail in the foregoing embodiments for the purpose of illustration, it is to be understood that such detail is solely for that purpose and that variations can be made therein by those skilled in the art without departing from the spirit and scope of the invention except as it may be described by the following claims.

What is claimed is:

1. An apparatus for treating a patient comprising:
    a radially expandable body having a proximal end, a distal end, a longitudinal axis therebetween, and a plurality of microstructures, each microstructure having first and second supports and a free end, the supports affixed to associate first and second adjacent portions of the radially expandable body, wherein the microstructures extend radially a distance of between 25 μm and 5000 μm from the radially expandable body,
    expansion of the expandable body within the patient effecting relative movement between the associated first and second portions of the expandable body,
    the relative movement deploying the microstructures from an undeployed position along the expandable body to a deployed position with the free end projecting radially outwardly from the expandable body.

2. An apparatus as in claim 1, wherein the relative movement of the associated first and second portions of the expandable body comprises circumferential movement of the first portion relative to the second portion when the expandable body expands radially.

3. An apparatus as in claim 2, wherein the associated first and second portions are in circumferential alignment and the circumferential movement of the first portion relative to the second portion draws the free end toward the circumferential alignment.

4. An apparatus as in claim 2, wherein the circumferential movement pulls the affixed ends of the first and second supports apart which moves the free end.

5. An apparatus as in claim 4, the radially expandable body further comprising an interior lumen along the longitudinal axis configured for receiving an expandable member which expands the expandable body, wherein the movement of the free end creates friction against the expandable member as the expandable member expands the expandable body, the friction projecting the free end radially outwardly.

6. An apparatus as in claim 4, the radially expandable body further comprising an interior lumen along the longitudinal axis configured for receiving an expandable member which expands the expandable body, wherein expansion of the expandable body by the expandable member pulls the affixed ends of the first and second supports apart which torsionally deforms the first and second supports projecting the free end radially outwardly.

7. An apparatus as in claim 4, wherein the radially expandable body is self-expanding composed and the self-expansion of the expandable body pulls the affixed ends of the first and second supports apart which torsionally deforms the first and second supports projecting the free end radially outwardly.

8. An apparatus as in claim 1, wherein each microstructure further comprises a third support affixed to an associated third portion of the radially expandable body, the associated first and third portions being connected so as to move in unison.

9. An apparatus as in claim 8, wherein the first, second and third supports comprise elongate shafts attached to the free end and to the associated first, second and third adjacent portions of the radially expandable body, respectively, and wherein the second support is disposed longitudinally between the first and third supports.

10. An apparatus as in claim 9, wherein the relative movement of the associated first and second portions of the expandable body comprises moving the associated first and second portions apart while the associated third portion moves in unison With the associated first portion, so that the supports pull the free end in opposite directions Forming a tripod structure which projects the free end radically outwardly.

11. A system for treating a patient comprising:
    An expandable body having a proximal end, a distal end, and at least one deployable microstructure, wherein expansion of the body deploys the at least one microstructure to project radially outward from the expandable body; and
    a material carried by the at least one microstructure, wherein the material is delivered to the patient by the at least one microstructure, wherein the at least one microstructure include a lumen and the material is held in the lumen; and
    wherein the expandable body further includes a delivery microsystem and the material is delivered to the lumen from the delivery microsystem; and
    wherein the delivery microsystem includes a therapeutic delivery control device which delivers the material to the lumen at predetermined intervals; and wherein delivery is triggered by an external signal in the form of a radiofrequency signal, an injectable chemical signal, an ultrasonic signal or a combination of these.

12. A method of treating a patient comprising the steps of:
providing an expandable body having a proximal end, a distal end, a longitudinal axis therebetween and at least one microstructure having an end attached to the body and a free end;
positioning the expandable body within a vessel of the patient, wherein the at least one microstructure is in an undeployed; and
expanding the body within the vessel so that forces are created which deploy the at least one microstructure, the free ends of the deployed microstructure projecting radially outward from the expandable body, wherein the at least one microstructure carries a material; and
further comprising delivering the material to the patient; and;
further comprising expandable the body so that the deployed at least one microstructure penetrates the vessel wall, wherein the material is held in a lumen within the at least one microstructure; and
delivering the material comprises injecting the material into the penetrated vessel wall.

13. a method for treating a patient comprising the steps of:
providing an expandable body having a proximal end, a distal end, and at least one deployable microstructure carrying a material;
positioning the expandable body in an undeployed position within a vessel of the patient;
expanding the body to a deployed position within the vessel, wherein expansion of the structure deploys the at least one microstructure to project radially outward from the expandable body;
penetrating a wall of the vessel with the at least one microstructure; and
delivering the material from the at least one microstructure to the wall of the vessel,
wherein the material is held in a lumen within the at least one microstructure, and delivering the material comprises injecting the material into penetrated vessel wall.

14. An apparatus for treating a patient comprising:
an expandable body having an inner ring an outer ring surrounding a longitudinal axis; and
at least one microstructure, each microstructure having first and second supports and a free end, the first support affixed to the inner ring and a second support affixed to the outer ring,
expansion of the expandable body within the patient effecting relative movement between the inner ring and the outer ring,
the relative movement deploying the at least one microstructure from an undeployed position to a deployed position with the free end projecting radially outwardly from the expandable body.

15. An apparatus as in claim 14, wherein the first and second supports are rotateably connected near the free end.

16. An apparatus as in claim 14, wherein the microstructures extend radially a distance between 25 µm and 5000 µm from the radially expandable body.

17. An apparatus as in claim 14, wherein the free end has a pointed shape.

18. An apparatus as in claim 17, wherein the pointed shape includes a single point, a multiple point, an arrow shaped point including a pointed tip and at least one undercut, or a combination of these.

19. An apparatus as in claim 14, further comprising a material carried by the at least one microstructure, wherein the material is delivered to the patient by the at least one microstructure.

20. An apparatus as in claim 19, wherein the material comprises at least a gene, at least a drug or a combination of these.

21. A method of treating a patient comprising the steps of:
providing an expandable body having a proximal end, a distal end, a longitudinal axis therebetween, an inner lumen and at least one microstructure having an end attached to the body, a free end and a protruding region therebetween which protrudes into the inner lumen;
positioning the expandable body within a vessel of the patient, wherein the at least one microstructure is in the undeployed position; and
applying a force against the protruding region from within the inner lumen which deploys the at least one microstructure to a deployed position wherein the free ends of the deployed microstructures project radially outwardly from the longitudinal axis.

22. A method as in claim 21, wherein applying a force against the protruding region comprises expanding an expandable member against the protruding region.

23. A method as in claim 22, wherein the expandable member comprises an inflatable member.

24. A method as in claim 21, wherein applying a force against the protruding region rotates the free end around the attached end.

25. A method as in claim 21, further comprising expanding the body so that the deployed at least one microstructure penetrates the vessel wall.

26. A method as in claim 25, wherein expanding the body comprises inflating an inflatable member within the body so as to increase its cross-sectional diameter.

27. A method as in claim 21, wherein the at least one microstructure carries a material and further comprising delivering the material to the patient.

28. A method as in claim 27, wherein the material comprises at least a gene, at least a drug or a combination of these.

* * * * *

UNITED STATES PATENT AND TRADEMARK OFFICE
CERTIFICATE OF CORRECTION

| | | |
|---|---|---|
| PATENT NO. | : 7,500,986 B2 | Page 1 of 1 |
| APPLICATION NO. | : 10/521078 | |
| DATED | : March 10, 2009 | |
| INVENTOR(S) | : Lye et al. | |

It is certified that error appears in the above-identified patent and that said Letters Patent is hereby corrected as shown below:

Column 18, line 47, "With the" should be changed to -- with the --

Signed and Sealed this

Tenth Day of November, 2009

David J. Kappos
*Director of the United States Patent and Trademark Office*